United States Patent [19]

Masaki et al.

[11] Patent Number: 5,070,089
[45] Date of Patent: Dec. 3, 1991

[54] THERAPEUTIC AGENT FOR LIVER DISEASE AND PIPERAZINE DERIVATIVES

[75] Inventors: Mitsuo Masaki, Chiba; Tomio Yamakawa, Kashiwa; Masaru Satoh, Koshigaya; Hiromitsu Takeda, Washimiya; Yasushi Yoshino, Narashino; Hitoshi Matsukura, Kasukabe, all of Japan

[73] Assignee: Nippon Chemiphar Co., Ltd., Tokyo, Japan

[21] Appl. No.: 302,552

[22] Filed: Jan. 26, 1989

[30] Foreign Application Priority Data

Jan. 26, 1988 [JP] Japan .................. 63-13622
Apr. 5, 1988 [JP] Japan .................. 63-84459
Apr. 5, 1988 [JP] Japan .................. 63-84460
Apr. 5, 1988 [JP] Japan .................. 63-84461

[51] Int. Cl.$^5$ .................. A01N 43/60; A61K 31/495; C07D 241/04
[52] U.S. Cl. .................. 514/255; 544/389
[58] Field of Search .................. 544/389; 514/255

[56] References Cited

U.S. PATENT DOCUMENTS 4,112,091 9/1978 Nesvadba .................. 544/389

FOREIGN PATENT DOCUMENTS 1810664 11/1969 Fed. Rep. of Germany .

OTHER PUBLICATIONS

Florvall, Dopamine β-hydroxylase Inhibitors, Acta Pharm, Sucecia 1970, 7(1)7–22.

Takemoto, N–Carbodithio, Derivatives of Piperazine, CA 55:27336, Yakugaku Kankyu 33 1–6 (1961).

Primary Examiner—Robert A. Wax
Assistant Examiner—Fred Tsung
Attorney, Agent, or Firm—McAulay Fisher Nissen Goldberg & Kiel

[57] ABSTRACT

A therapeutic agent for liver disease containing as an active ingredient a piperazine derivative having the formula:

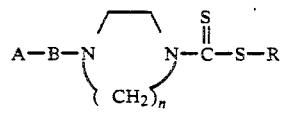

wherein, A represents a phenyl, p-benzoquinonyl or cumarinyl group which may have at least one substituent selected from the group consisting of halogen, alkyl, fluoroalkyl, formyl, alkoxycarbonyl, acyl, hydroxy, alkoxy, acyloxy, glycosyloxy, amino, alkylamino, mercapto, alkylthio and nitro; B represents a single bond or a straight chain alkylene group containing 1–4 carbon atoms which may have at least one substituent selected from the group consisting of alkyl, aryl, aralkyl, hydroxy and oxo; R represents an atom or a group selected from the group consisting of hydrogen, alkali metal, alkaline earth metal, alkyl, cycloalkyl, aralkyl and aryl; and n is 2 or 3, or its pharmaceutically acceptable salt is disclosed.

6 Claims, No Drawings

THERAPEUTIC AGENT FOR LIVER DISEASE AND PIPERAZINE DERIVATIVES

BACKGROUND OF THE INVENTION

1. Field of the Invention

The present invention relates to a novel therapeutic agent for treatment or prevention of liver disease and a novel piperazine derivative.

2. Description of Prior Art

Liver is an organ showing various functions such as detoxication, carbohydrate metabolism, lipid metabolism, protein metabolism, production and secretion of bile, production of blood coagulation factors, control of production of hormones, and storage of various materials employed for constituting a living body such as fat, glycogen, protein and vitamine. These functions of liver may suffer from acute or chronic damages by action of virus, medicaments, toxic material, alcohol, malnutrition, damage of liver circulation system or bile thrombus. Such damages causes various diseases such as virus hepatitis, hepatitis caused by toxicity of medicaments, alcoholic hepatitis, congestive hepatitis, cholangiolitic hepatitis, fatty liver an jaundice. Such diseases may finally cause liver cirrhosis.

Accordingly, studies have been heretofore made for the purpose of finding medicaments for treatment or prevention of liver disease. Based on these studies, a number of therapeutic agents for liver disease have been developed and employed in practice. Representative examples of the known therapeutic agents for liver disease include Malotilate (diisopropyl 1,3-dithiol-2-ylidene malonate), Catergen ((2R,3S)-2-(3,4-dihydroxyphenyl)-3,4-dihydro-2H-1-benzopyran-3,5,7-triol), and Glycyrrhizin (20$\beta$-carboxy-11-oxo-30-norolean-12-en-3$\beta$-yl-2-O-$\beta$-D-glucopyranuronosyl-$\alpha$-D-glucopyranosiduronic acid).

The present inventors have made study on piperazine derivatives and have discovered that specific piperazine derivatives and their pharmaceutically acceptable salts are effective for prevention and/or treatment of liver disease.

There are known a great number of piperazine derivatives. However, there is known no pharmacogical effect of piperazine derivative as therapeutic agent for liver disease, so long as compounds analogous to the specific piperazine derivatives found by the present inventors. For instance, 4-(2-phenylalkyl)-1-piperazinecarbodithio acid and its alkyl ester is disclosed in Acta Pharm. Suecica, 7(1), 7–22 (1970). However, no pharmacological effect for prevention or treatment of liver disease is suggested. Further, 4-(6,7-dihydoxycumarin-8-yl)methyl-1-piperazine-ethanol is disclosed in Zh. Obshch. Khim. 33(3), 793–7 (1966); 4-{2-(3,4-dihydroxyphenyl)-2-oxo}-ethyl-1-piperazine-ethanol is disclosed in Latv. PSR Zinat. Akad. Vestis, kim. Ser., (5), 593–6 (1968); and 4-{2-(3,4-dihydroxyphenyl)-2-oxo}ethyl-1-methylpyperazine is disclosed in Arzneim.-Forsch., 19(10), 1698–1702 (1969). Nevertheless, there is neither disclosure nor suggestion to indicate pharacological effect of the disclosed piperazine derivatives with respect to prevention or treatment of liver disease.

SUMMARY OF INVENTION

A principal object of the present invention is to provide a novel therapeutic agent for treatment of liver disease.

Another object of the invention is to provide an agent for inhibitory effect on lipid peroxidation.

A further object of the invention is to provide an agent having a function of trapping active oxygen produced in a living body.

There is provided by the present invention a novel therapeutic agent for liver disease containing as an active agent a piperazine derivative having the formula (I):

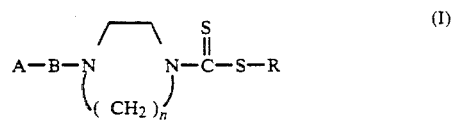

wherein

A represents a phenyl, p-benzoquinonyl or cumarinyl group which may have at least one substituent selected from the group consisting of halogen, alkyl, fluoroalkyl, formyl, alkoxycarbonyl, acyl, hydroxy, alkoxy, acyloxy, glycosyloxy, amino, alkylamino, mercapto, alkylthio and nitro;

B represents a single bond or a straight chain alkylene group containing 1–4 carbon atoms which may have at least one substituent selected from the group consisting of alkyl, aryl, aralkyl, hydroxy and oxo;

R represents an atom or a group selected from the group consisting of hydrogen, alkali metal, alkaline earth metal, alkyl, cycloalkyl, aralkyl and aryl; and n is 2 or 3, or its pharmaceutically acceptable salt.

The above-identified piperazine derivative having the formula (I) and its pharmaceutically acceptable salt show favorable action in in-vivo tests for treatment acute liver disease caused by carbon tetrachloride for inhibition or suppresion of deviation of values of GOT (glutamic-oxaloacetic transaminase) and GPT (glutamic-pyruvic transaminase).

Accordingly, the piperazine derivative of the formula (I) and its pharmaceutically acceptable salt according to the invention are well effective for prevention or treatment (including treatment for suppresion of disease) of liver disease.

The piperidine derivative of the formula (I) and its pharmaceutically acceptable salt further shows inhibitory effect on lipid peroxidation as well as an action for trapping an active oxygen. It is known that increase of the lipid peroxide is closely related to diseases of various organs in a living body. Further, it is known that increase of the lipid peroxide is also observed when a living body gets old, is exposed to radioactive rays, or takes medicaments. Therefore, it is considered that the increase of lipid peroxide is related to aging and cancer. For this reason, a substance having inhibitory effect on lipid peroxidation is active not only as a therapeutic agent for liver disease but also as a therapeutic agent for treating inflammation, rheumatism, disease of digestive tract, cataract, arteriosclerosis, cerebral infraction, or autoimmune disease.

Further, there is provided by the invention a novel piperazine derivative having the formula (II):

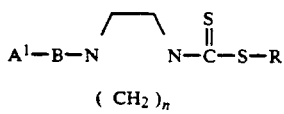

(II)

wherein
- $A^1$ represents a phenyl group which has at least one substituent selected from the group consisting of halogen, alkyl, fluoroalkyl, formyl, alkoxycarbonyl, acyl, hydroxy, alkoxy, acyloxy, glycosyloxy, amino, alkylamino, mercapto, alkylthio and nitro, or a p-benzoquinonyl or cumarinyl group which may have at least one substituent selected from the above group;
- B represents a single bond or a straight chain alkylene group containing 1-4 carbon atoms which may have at least one substituent selected from the group consisting of alkyl, aryl, aralkyl, hydroxy and oxo;
- R represents an atom or a group selected from the group consisting of hydrogen, alkali metal, alkaline earth metal, alkyl, cycloalkyl, aralkyl and aryl; and
- n is 2 or 3.

DETAILED DESCRIPTION OF THE INVENTION

In the above-mentioned formula (I), A represents one of phenyl group, p-benzoquinonyl group and cumarinyl group. These groups may have one or more substituents such as halogen (e.g., chlorine, bromine or fluorine), alkyl having 1-6 carbon atoms (e.g., methyl, ethyl, propyl or butyl), fluoroalkyl having 1-6 carbon atoms (e.g., trifluoromethyl), formyl, alkoxycarbonyl having 2-7 carbon atoms (e.g., methoxycarbonyl or ethoxycarbonyl), acyl having 2-7 carbon atoms (e.g., acetyl or propionyl), hydroxy, alkoxy having 1-6 carbon atoms (e.g., methoxy, ethoxy or propoxy), acyloxy having 2-7 carbon atoms (e.g., acetoxy or propionyloxy), glycosyloxy (e.g., glycofuranosyloxy, glycopyranosyloxy or glycoseptanosyloxy), amino, alkylamino having 1-6 carbon atoms (e.g., monoalkylamino such as monomethylamino or monoethylamino or dialkylamino such as dimethylamino or diethylamino), mercapto, alkylthio having 1-6 carbon atoms (e.g., methylthio, ethylthio or propylthio), and nitro.

The phenyl, p-benzoquinonyl or cumarinyl group may have one to five substituents on their rings. In the case that the group has two or more substituents, these substituents may be the same as or different from each other. In the case that a substituent is attached to a phenyl group, the substituent is preferably attached to the ortho-position with respect to the position to which the bonding or group of "B" is combined. In the case that two hydroxy groups are attached to a phenyl group at adjoining positions, these hydroxy may be combined via methylene to form —O—CH$_2$—O— bonding.

In the above-mentioned formula (II), $A^1$ represents a phenyl which necessarily has one or more substituents such as halogen (e.g., chlorine, bromine or fluorine), alkyl having 1-6 carbon atoms (e.g., methyl, ethyl, propyl or butyl), fluoroalkyl having 1-6 carbon atoms (e.g., trifluromethyl), formyl, alkoxycarbonyl having 2-7 carbon atoms (e.g., methoxycarbonyl or ethoxycarbonyl), acyl having 2-7 carbon atoms (e.g., acetyl or propionyl), hydroxy, alkoxy having 1-6 carbon atoms (e.g., methoxy, ethoxy or propoxy), acyloxy having 2-7 carbon atoms (e.g., acetoxy or propionyloxy), glycosyloxy (e.g., glycofuranosyloxy, glycopyranosyloxy (e.g., α-D-glucopyranosyloxy, α-D-galactopyranosyloxl or β-arabinopyranosyloxy) or glycoseptanosyloxy), amino, alkylamino having 1-6 carbon atoms (e.g., monoalkylamino such as monomethylamino or monoethylamino or dialkylamino such as dimethylamino or diethylamino), mercapto, alkylthio having 1-6 carbon atoms (e.g., methylthio, ethylthio or propylthio), and nitro.

The phenyl group for "$A^1$" in the formula (II) should have one to five substituents selected from the above listed atoms and groups.

The p-benzoquinonyl or cumarinyl group for "$A^1$" in the formula (II) may have no substituent or may have one or more substituents selected from the above listed atoms and groups.

In the case that the phenyl, p-benzoquinonyl or cumarinyl group has two or more substituents, these substituents may be the same as or different from each other. In the case that a substituent is attached to a phenyl group, the substituent is preferably attached to the ortho-position with respect to the position to which the bonding or group of "B" is combined. In the case that two hydroxy groups are attached to a phenyl group at adjoining positions, these hydroxy may be combined via methylene to form —O—CH$_2$—O— bonding.

In the formulae (I) and (II), B represents a single bond or a straight chain alkylene group containing 1-4 carbon atoms. The straight chain alkylene group may have ore or more substituents such as alkyl having 1-4 carbon atoms (e.g., methyl, ethyl or propyl), aryl (e.g., phenyl) which may have one or more substituents (e.g., alkyl such as methyl or ethyl, alkoxy such as methoxy or ethoxy, or halogen such as fluorine, chlorine or bromine), aralkyl (e.g. benzyl) which may have one or more substituents as mentioned for the possible substituents of the alkyl, hydroxy and oxo. In the piperazine derivative of the invention, B preferably is a straight chain alkylene having 1-4 carbon atoms which may have one or more substituents selected from the group consisting of phenyl benzyl, hydroxy and oxo.

In the formulae (I) and (II), R represents hydrogen, alkali metal (e.g., sodium or potassium), alkaline earth metal (e.g., calcium or magnesium), alkyl having 1-6 carbon atoms (e.g., methyl, ethyl, propyl or butyl), cycloalkyl (e.g., cyclopentyl or cyclohexyl), aralkyl (e.g., benzyl or benzhydryl), or aryl (e.g., phenyl, tolyl or xylyl). In the invention, R preferably is alkyl.

In the formulae (I) and (II), "n" is 2 or 3, and "n" preferably is 2.

Preferred groups and atoms for "A", "$A^1$", B and R are described below.

Each of "A" in the formula (I) and "$A^1$" in the formula (II) preferably is a phenyl group having at least one substituent selected from the group consisting of hydroxy, alkoxy, acyloxy, amino, alkylamino, alkylthio, halogen, alkyl and nitro.

Further, each of "A" in the formula (I) and "$A^1$" in the formula (II) preferably is a phenyl group having at least one substituent selected from the group consisting of hydroxy and alkoxy and additionally having at least one substituent selected from the group consisting of halogen, alkyl, fluoroalkyl, formyl, alkoxycarbonyl, acyl, acyloxy, glycosyloxy, amino, alkylamino, mercapto, alkylthio, and nitro.

Furthermore, each of "A" in the formula (I) and "$A^1$" in the formula (II) preferably is a p-benzoquinonyl or cumarinyl group which have at least one substituent selected from the group consisting of alkyl and alkoxy.

The piperidine derivatives of the formulae (I) and (II) in which R is hydrogen, alkyl, cycloalkyl, aryl or aralkyl may be produced in the form of their pharmaceutically acceptable addition salt. Such addition salts can be prepared using hydrochloric acid, hydrobromic acid, sulfuric acid, furaric acid, maleic acid or tartaric acid. Other inorganic or organic acids can be employed, so long as such acids can give pharmacologically acceptable salts with the piperizine derivatives of the invention.

The piperizine derivatives of the formulae (I) and (II) can be prepared, for instance, by the following processes.

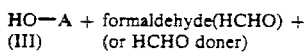
HO—A + formaldehyde(HCHO) +       (1)
(III)      (or HCHO doner)

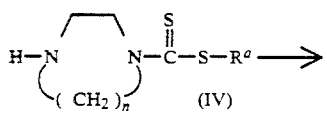
(IV)

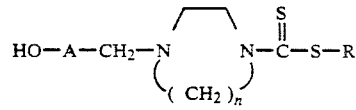

In the above equation, A represents a phenyl or cumarinyl group which may have at least one substituent such as halogen, alkyl, fluoroalkyl, formyl, alkoxycarbonyl, acyl, hydroxy, alkoxy, acyloxy, glycosyloxy, amino, alkylamino, mercapto, alkylthio and nitro; R$^a$ is hydrogen, alkyl, cycloalkyl, aralkyl and aryl; and n is 2 or 3.

The reaction of the compounds of the above formulae (III) and (IV) and formaldehyde (or formaldehyde doner) can be performed under appropriate conditions according to the known Mannich reaction. In the equation, a piperazine derivative of the formula (IV) may be in the form of an addition salt such as hydrochloride. Formaldehyde (or formaldehyde doner) may be used in the form of aqueous formalin or paraformaldehyde. The reaction according to the equation can be carried out in water, an alcoholic solvent such as methanol or ethanol, an organic acid such as acetic acid, an etheral solvent such as ether or dioxane, or other polar solvent such as dimethylformamide (DMF) or acetonitrile at a temperature ranging from 0° C. to the boiling point of the used solvent.

Alternatively, an active compound produced by a reaction of a piperazine derivative of the formula (IV) and formaldehyde can be caused to react with a compound of the formula (III) to yield a compound of the formula (I). The above-mentioned active compound can be represented by one of the following formulae:

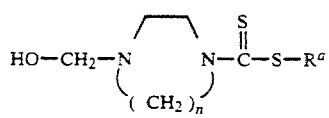
(IVa)

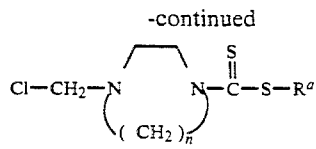
(IVb)

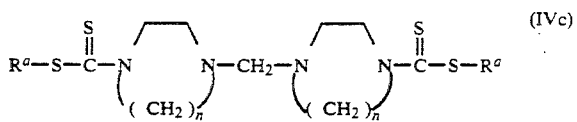
(IVc)

In the above formulae, each of R$^a$ and "n" has the same meaning as above.

    (2)

(V)    (VI)

In the above formulae, Q$^1$ is a releasable group, and each of A$^1$, B, R and "n" has the same meaning as above.

In the above equation, the reaction between a compound of the formula (V) and a piperazine derivative of the formula (VI) can be performed in an inert solvent such as ethanol, acetone, methylene chloride or DMF in the presence of a base such as sodium carbonate, potassium carbonate, sodium hydroxide or triethylamine. The reaction can be carried out at a temperature of 0° C. to the boiling point of the employed solvent. The reaction, alternatively, can be performed under heating to 50° to 250° C. in the absence of a solvent. Examples of the releasable groups represented by Q$^1$ include halogen atoms such as chlorine and bromine and tosyloxy group.

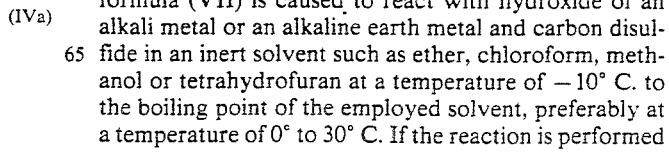    (3)

(VII)

(VIII)

In the above formulae, M is an alkali metal or an alkaline earth methal, and each of A$^1$, B, and "n" has the same meaning as above.

In the above equation, a piperazine derivative of the formula (VII) is caused to react with hydroxide of an alkali metal or an alkaline earth metal and carbon disulfide in an inert solvent such as ether, chloroform, methanol or tetrahydrofuran at a temperature of −10° C. to the boiling point of the employed solvent, preferably at a temperature of 0° to 30° C. If the reaction is performed using neither hydroxide of alkali metal nor alkaline earth metal, a piperazine derivative of the formula (VIII) is obtained in the form where the alkali metal or alkaline earth metal is replaced with hydrogen.

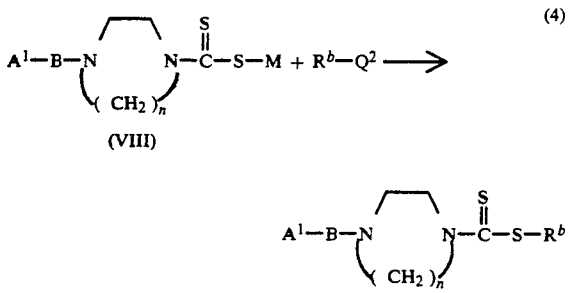

In the above formulae, $Q^2$ is a releasable group, $R^b$ is alkyl, cycloalkyl, aralkyl or aryl, and each of $A^1$, B, M and "n" has the same meaning as above.

In the above equation, the reaction can be performed in an inert solvent such as methanol, ethanol, DMF, tetrahydrofuran, chloroform or benzene at a temperature of $-10°$ C. to the boiling point of the employed solvent, preferably at a temperature of $0°$ to $30°$ C. Examples of the releasable groups represented by $Q^2$ include halogen atoms such as chlorine, bromine and iodine, p-toluenesulfonyloxy and methansulfonyloxy. Even if a piperazine derivative of the formula (VIII) where the alkali metal or alkaline earth metal is replaced with hydrogen is used as the starting compound, the reaction can be carried out in the presence of an alkali metal in a similar manner.

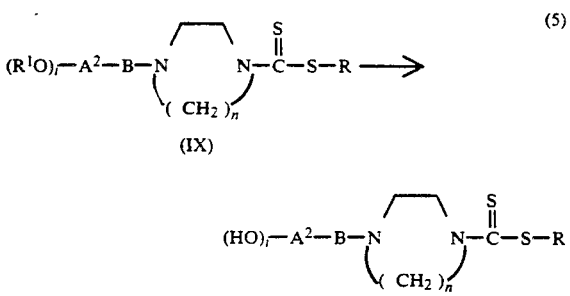

In the formulae, $R^1$ is alkyl, "i" is an integer of 1 to 5, $A^2$ corresponds to the aforementioned "A" except for excluding both the alkoxy- and alkoxycarbonyl-substituted groups, and each of B, R and "n" has the same meaning as above.

In the above equation, the reaction can be performed by cleaving the ether group of the piperizine derivative of the formula (IX) using an appropriate reagent to convert the alkoxy group (which is attached to the group "$A^2$") into hydroxy. Examples of the reagent for cleaving the ether group include boron tribromide, hydrobromic acid, trimethylsilane iodide and pyridine hydrochloride. Preferred is boron tribromide. If boron tribromide is employed in the reaction, the reaction can be performed in an alkyl halide solvent such as methylene chloride or chloroform at a temperature of $-70°$ C. to $30°$ C., preferably at a temperature of $-50°$ C. to $0°$ C. for a period of time of 1 hr. to 5 days, preferably for a period of time of 5 hrs. to 2 days.

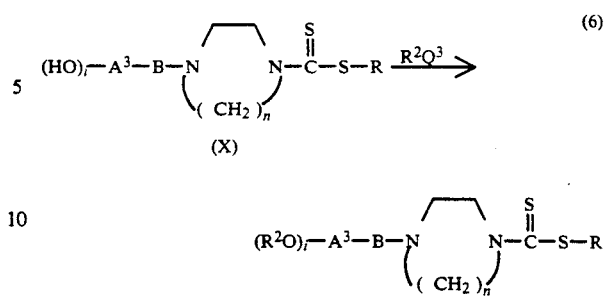

In the above formulae, $R^2$ is alkyl or acyl, $Q^3$ is a releasable group "i" is an integer of 1 to 5, $A^3$ corresponds to the aforementioned "$A^1$" except for excluding the hydroxy-substituted group, and each of B, R and "n" has the same meaning as above.

In the above equation, the reaction can be performed by converting the hydroxy group attached to the group of "$A^3$" of the piperizine derivative of the formula (X) into alkoxy or acyloxy. The reaction can be carried out by acylating or alkylating the piperizine derivative of the formula (X) in an inert solvent such as chloroform using an appropriate reagent. The acylating reagent may be acetic anhydride and the alkylating reagent may be dialkylsulfuric acid.

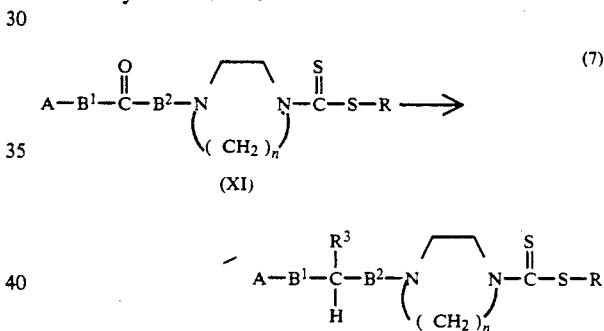

In the formulae, each of $B^1$ and $B^2$ independently is a straight chain alkylene group having 1-3 carbon atoms which may be substituted with alkyl, aryl or aralkyl but is not substituted with hydroxy or oxo, provided that the total number of carbon atoms contained in the straight chain alkylene groups of $B^1$ and $B^2$ does not exceed 4 ($B^1$ may be a simple linking bond), $R^3$ is hydroxy or hydrogen, and each of A, R and "n" has the same meaning as above.

In the above equation, the reaction can be performed by reducing the $>C=O$ group of the piperizine derivative of the formula (XI) in a solvent generally employable for reducing reactions using a reducing agent. Examples of the solvent include methanol, ethanol and tetrahydrofuran (THF). Examples of the reducing agent include sodium borohydride, and sodium borohydride-aluminum chloride.

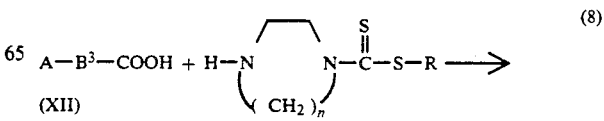

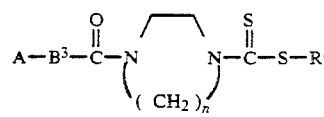

In the above formulae, $B^3$ is a simple linking bond or a straight chain alkylene group having 1-3 carbon atoms which may be substituted alkyl, aryl, aralkyl, hydroxy or oxo, and each of A, $R^a$ and "n" has the same meaning as above.

In the above equation, the reaction is performed by subjecting a carboxylic acid of the formula (XII) and the piperazine derivative to dehydrating condensation. The dehydrating condensation can be carried out using a known condensating agent such as dicyclohexylcarbodiimide. Alternatively, the condensation can be carried out after converting the carboxylic acid into its reactive derivative.

In addition, the piperazine derivative of the formula (I) can be prepared by the following process.

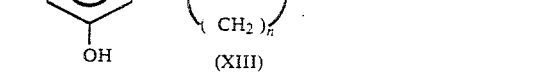

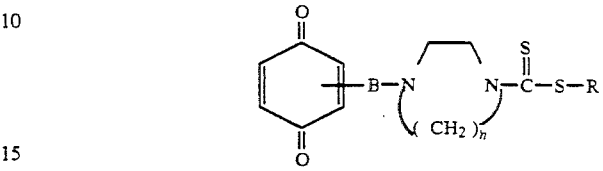

In the above equation, the reaction is performed employing an oxidizing agent such as $FeCl_3$. Also employable are nitric acid, silver oxide, lead tetraacetate, alkaline salts of dichromic acid and lead oxide.

Representative examples of the piperazine derivative of the formula (I) are set forth in the following Table 1 and Table 2. In the Tables, each symbol means the following group: Me: methyl, Et: ethyl, Pr: propyl, cy-hex: cyclohexyl, Ph: phenyl, Ac: acetyl, and Glu: glucopyranosyl.

TABLE 1

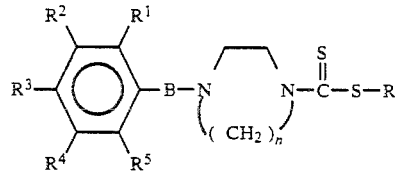

| No. | $R^1$ | $R^2$ | $R^3$ | $R^4$ | $R^5$ | B | n | R |
|---|---|---|---|---|---|---|---|---|
| 1 | H | H | H | H | H | $CH_2$ | 2 | Me |
| 2 | Cl | H | H | H | H | $CH_2$ | 2 | Me |
| 3 | Me | H | H | H | H | $CH_2$ | 2 | Me |
| 4 | OH | H | H | H | H | $CH_2$ | 2 | Me |
| 5 | OMe | H | H | H | H | $CH_2$ | 2 | Me |
| 6 | H | OMe | H | H | H | $CH_2$ | 2 | Me |
| 7 | H | H | OMe | H | H | $CH_2$ | 2 | Me |
| 8 | SH | H | H | H | H | $CH_2$ | 2 | Me |
| 9 | SMe | H | H | H | H | $CH_2$ | 2 | Me |
| 10 | $NO_2$ | H | H | H | H | $CH_2$ | 2 | Me |
| 11 | $NH_2$ | H | H | H | H | $CH_2$ | 2 | Me |
| 12 | NHMe | H | H | H | H | $CH_2$ | 2 | Me |
| 13 | $NMe_2$ | H | H | H | H | $CH_2$ | 2 | Me |
| 14 | OAc | H | H | H | H | $CH_2$ | 2 | Me |
| 15 | OH | OH | H | H | H | $CH_2$ | 2 | Me |
| 16 | OH | H | H | OH | H | $CH_2$ | 2 | Me |
| 17 | OH | H | H | H | OH | $CH_2$ | 2 | Me |
| 18 | OH | OMe | H | H | H | $CH_2$ | 2 | Me |
| 19 | OH | H | OMe | H | H | $CH_2$ | 2 | Me |
| 20 | OH | H | H | OMe | H | $CH_2$ | 2 | Me |
| 21 | OH | H | H | OAc | H | $CH_2$ | 2 | Me |
| 22 | OMe | OMe | H | H | H | $CH_2$ | 2 | Me |
| 23 | OMe | H | H | OMe | H | $CH_2$ | 2 | Me |
| 24 | OMe | H | H | H | OMe | $CH_2$ | 2 | Me |
| 25 | OMe | H | Me | H | H | $CH_2$ | 2 | Me |
| 26 | OMe | H | $CF_3$ | H | H | $CH_2$ | 2 | Me |
| 27 | OMe | H | H | H | Me | $CH_2$ | 2 | Me |
| 28 | OMe | H | Cl | H | H | $CH_2$ | 2 | Me |
| 29 | OMe | H | H | Ac | H | $CH_2$ | 2 | Me |
| 30 | SMe | H | H | OMe | H | $CH_2$ | 2 | Me |
| 31 | H | OMe | OMe | H | H | $CH_2$ | 2 | Me |
| 32 | OH | OH | OH | H | H | $CH_2$ | 2 | Me |
| 33 | OMe | OMe | OMe | H | H | $CH_2$ | 2 | Me |
| 34 | OAc | OAc | OAc | H | H | $CH_2$ | 2 | Me |
| 35 | OH | OMe | OMe | H | H | $CH_2$ | 2 | Me |
| 36 | OMe | H | OMe | H | OMe | $CH_2$ | 2 | Me |
| 37 | OH | H | OMe | H | OMe | $CH_2$ | 2 | Me |
| 38 | OH | OMe | H | CHO | H | $CH_2$ | 2 | Me |
| 39 | OH | OH | H | $CO_2Me$ | H | $CH_2$ | 2 | Me |

TABLE 1-continued

| No. | R¹ | R² | R³ | R⁴ | R⁵ | B | n | R |
|---|---|---|---|---|---|---|---|---|
| 40 | H | OH | OH | OH | H | CH$_2$ | 2 | Me |
| 41 | H | OMe | OMe | OMe | H | CH$_2$ | 2 | Me |
| 42 | H | OAc | OAc | OAc | H | CH$_2$ | 2 | Me |
| 43 | H | OMe | OH | OMe | H | CH$_2$ | 2 | Me |
| 44 | OH | OH | OH | H | CO$_2$Pr | CH$_2$ | 2 | Me |
| 45 | OMe | OMe | OMe | H | CO$_2$Pr | CH$_2$ | 2 | Me |
| 46 | OH | Me | Me | OH | Me | CH$_2$ | 2 | Me |
| 47 | OH | OMe | OMe | OH | Me | CH$_2$ | 2 | Me |
| 48 | OAc | OMe | OMe | OAc | Me | CH$_2$ | 2 | Me |
| 49 | OH | H | H | H | H | CO | 2 | Me |
| 50 | OH | H | H | OH | H | CO | 2 | Me |
| 51 | OMe | H | H | H | H | CO | 2 | Me |
| 52 | SMe | H | H | H | H | CO | 2 | Me |
| 53 | OMe | OMe | H | H | H | CO | 2 | Me |
| 54 | OMe | H | OMe | H | H | CO | 2 | Me |
| 55 | OMe | H | H | OMe | H | CO | 2 | Me |
| 56 | OMe | OMe | OMe | H | H | CO | 2 | Me |
| 57 | H | OMe | OMe | OMe | H | CO | 2 | Me |
| 58 | H | —OCH$_2$O— | | H | H | CO | 2 | Me |
| 59 | NH$_2$ | H | H | H | H | CO | 2 | Me |
| 60 | NMe$_2$ | H | H | H | H | CO | 2 | Me |
| 61 | OAc | OAc | OAc | H | H | CO | 2 | Me |
| 62 | OMe | OMe | OMe | H | H | CO | 2 | Et |
| 63 | OMe | H | H | H | H | CH$_2$CH$_2$ | 2 | Me |
| 64 | OH | H | H | H | H | CH$_2$CH$_2$ | 2 | Me |
| 65 | OMe | H | H | Cl | H | CH$_2$CH$_2$ | 2 | Me |
| 66 | OMe | H | H | OAc | H | CH$_2$CH$_2$ | 2 | Me |
| 67 | OMe | OMe | OMe | H | H | CH$_2$CH$_2$ | 2 | Me |
| 68 | OH | OH | OH | H | H | CH$_2$CH$_2$ | 2 | Me |
| 69 | OMe | OMe | OMe | H | H | — | 2 | Me |
| 70 | H | OMe | OMe | OMe | H | — | 2 | Me |
| 71 | OMe | OMe | OMe | H | H | COCH$_2$ | 2 | Me |
| 72 | H | OH | OH | H | H | COCH$_2$ | 2 | Me |
| 73 | H | OH | OH | H | H | CH(OH)CH$_2$ | 2 | Me |
| 74 | H | OMe | OMe | OMe | H | COCH$_2$ | 2 | Me |
| 75 | OMe | OMe | OMe | H | H | CH$_2$CO | 2 | Me |
| 76 | H | OH | OH | H | H | CH$_2$CO | 2 | Me |
| 77 | OH | H | H | H | H | CH$_2$CO | 2 | Me |
| 78 | NH$_2$ | H | H | H | H | CH$_2$CO | 2 | Me |
| 79 | NMe$_2$ | H | H | H | H | CH$_2$CO | 2 | Et |
| 80 | H | —OCH$_2$O— | | H | H | CH$_2$CO | 2 | Me |
| 81 | OMe | H | H | H | H | CH$_2$CH$_2$CH$_2$ | 2 | Me |
| 82 | OMe | OMe | OMe | H | H | CH$_2$CH$_2$CH$_2$ | 2 | Me |
| 83 | OH | H | H | OH | H | CH$_2$CH$_2$CO | 2 | Me |
| 84 | OMe | OMe | OMe | H | H | CH$_2$CH$_2$CO | 2 | Me |
| 85 | H | —OCH$_2$O— | | H | H | CH$_2$CH$_2$CO | 2 | Et |
| 86 | OH | H | H | H | H | CHOHCH$_2$CO | 2 | Me |
| 87 | OMe | OMe | OMe | H | H | (CH$_2$)$_3$CO | 2 | Me |
| 88 | OMe | OMe | OMe | H | H | CH$_2$ | 3 | Me |
| 89 | H | OMe | OMe | OMe | H | CH$_2$ | 2 | Na |
| 90 | OMe | OMe | OMe | H | H | CH$_2$ | 2 | Na |
| 91 | OMe | OMe | OMe | H | H | CH$_2$ | 2 | K |
| 92 | OH | OH | OH | H | H | CH$_2$ | 2 | H |
| 93 | OMe | OMe | OMe | H | H | CH$_2$ | 2 | H |
| 94 | H | OMe | OMe | OMe | H | — | 2 | H |
| 95 | OMe | OMe | OMe | H | H | CH$_2$ | 2 | Et |
| 96 | H | OMe | OMe | OMe | H | CH$_2$ | 2 | i-Pr |
| 97 | OMe | OMe | OMe | H | H | CH$_2$ | 2 | Pr |
| 98 | OMe | H | H | H | H | CH$_2$ | 2 | cy-hex |
| 99 | H | OMe | OMe | OMe | H | CH$_2$ | 2 | CH$_2$Ph |
| 100 | OH | OH | OH | H | H | CH$_2$ | 2 | CH$_2$Ph |
| 101 | OMe | OMe | OMe | H | H | CH$_2$ | 2 | Ph |
| 102 | H | H | H | H | H | CHPh | 2 | Me |
| 103 | OMe | H | H | H | H | CHPh | 2 | Me |
| 104 | OH | H | H | H | H | CHPhCH$_2$ | 2 | Me |
| 105 | OMe | H | H | H | H | CH(CH$_2$Ph) | 2 | Me |
| 106 | OH | OH | H | —CH=CHCO$_2$— | | CH$_2$ | 2 | Me |
| 107 | OH | OGlu | H | —CH=CHCO$_2$— | | CH$_2$ | 2 | Me |
| 108 | H | OMe | OMe | OMe | H | CH$_2$ | 2 | H |
| 109 | H | OH | OH | OH | H | CH$_2$ | 2 | H |

TABLE 2

$$R^1 \underset{R^2}{\overset{O}{\underset{\|}{\bigcirc}}} \underset{R^3}{\overset{\|}{\underset{O}{\bigcirc}}} B-N\underset{(CH_2)_n}{\diagup}N-\overset{S}{\underset{\|}{C}}-S-R$$

| No. | $R^1$ | $R^2$ | $R^3$ | B | n | R |
|---|---|---|---|---|---|---|
| 110 | H | H | H | $CH_2$ | 2 | Me |
| 111 | Me | H | H | $CH_2$ | 2 | Me |
| 112 | Me | Me | H | $CH_2$ | 2 | Me |
| 113 | Me | Me | Me | $CH_2$ | 2 | Me |
| 114 | H | H | H | $CH_2CH_2$ | 2 | Me |
| 115 | H | H | H | $CH_2CO$ | 2 | Me |
| 116 | Me | Me | Me | $CH_2$ | 3 | Me |
| 117 | Me | Me | Me | $CH_2$ | 2 | Pr |
| 118 | OMe | OMe | Me | $CH_2$ | 2 | Me |
| 119 | OMe | OMe | Me | $CH_2$ | 2 | $CH_2Ph$ |
| 120 | OMe | OMe | Cl | $CH_2CH_2CH_2$ | 2 | Me |

The inhibitory action on lipid peroxidation of the piperazine derivatives of the invention is illustrated by the following pharmacological experimental data. Further, the preventive action on deviation of GOT value and GPT value determined using acute liver disease model in vivo is shown below.

EXPERIMENT 1

Inhibitory Action on Lipid Peroxidation

1. Experimental procedure

A hepatocyte was isolated from rat according to the method of Ui et al (Hiroshi Oka and Tadao Ui: "Isolated Cells—Experimental and Application", page 91). The determination of lipid peroxidation was performed using a died hepatocyte which had been frozen at $-85°$ C. and stored at the temperature and which was melted when the experimental was done.

To 50 μl of a hepatocyte dispersion (amount of protein: 0.5–1.0 mg) in a centrifugal tube were successively added 5 μl of a DMSO (dimethylsulfoxide) solution of the sample compound, 50 μl of ADP solution (40 mmol.), 50 μl of NADPH solution (4 mmol.) and 350 μl of Tris(0.5 mol.)-hydrochloric acid buffer (pH 7.4). The centrifugal tube was shaken at 37° C. for 1 hour for performing a reaction, and then placed into an ice-water bath to terminate the reaction. To the content of the centrifugal tube were added 0.2 ml of 8.1% aqueous SDS (sodium dodecylsulfonate) solution, 50 μl of ethanol solution of BHT (2,6-di-tert-butyl-p-cresol, 5,000 ppm), 1.8 ml of 20% acetic acid (pH 3.5) and 1.5 ml of 0.8% TBA (thiobarbituric acid) solution (pH 3.5). The centrifugal tube was taken out of the ice-water bath and placed in a water bath (kept at 95°–98° C.). The content of the tube was heated in the bath for 1 hour for developing color-formation. After the heating was complete, the content of the tube was cooled and subjected to centrifugal separation. The inhibitory action on lipid peroxidation of the sample was determined by measuring absorbance at 530 nm. The determined inhibitory action is expressed inhibition ratio by percent (%) calculated by the following equation:

Inhibition Ratio (%) =

[1 − (absorbance of tested compound-applied group − absorbance of blank group)/(absorbance of control group − absorbance of blank group)] × 100

Remark: To the control group was applied (added) DMSO only.

2. Results

The results of the determination are set forth in Table 3. In Table 3, the number of the tested compound corresponds to the identical number set forth in Tables 1 and 2 for identifying the compounds of the invention.

TABLE 3

| No. of Tested Compound | Inhibition ratio (at Final Concentration of Tested Compound) | |
|---|---|---|
| | $10^{-4}$M | $10^{-5}$M |
| 89 | 90.2% | — |
| 40 | 92.6 | — |
| 106 | 89.0 | 88.1% |
| 72 | 74.8 | 58.2 |
| 73 | 88.4 | 44.5 |
| 108 | 72.6 | 39.2 |
| 42 | 71.6 | 71.6 |
| 16 | 73.4 | 69.4 |
| 32 | 87.8 | 87.4 |
| 109 | 74.9 | 24.2 |
| 4 | 100 | 96.6 |
| 44 | 96.6 | 96.0 |
| 13 | 98.9 | 95.4 |
| 22 | 100 | 92.0 |
| 47 | 100 | 56.1 |
| 23 | 100 | 60.6 |
| 11 | 98.6 | 95.5 |
| 48 | 96.2 | 97.5 |

It is apparent from the results given in Table 3 that the piperazine derivatives of the present invention show excellent inhibitory action on enzymic lipid peroxidation in vitro.

EXPERIMENT 2

Preventive Action on Deviation of GOT Value and GPT Value In Vivo Using Model of Acute Liver Disease Caused by $CCl_4$ 1. Experimental procedure $CCl_4$ in olive oil (concentration: 50%) was orally administered to a Wister-strain rat (body weight: 170–180 g) fasted for 24 hrs., at a dose of 1 ml/kg, to cause acute liver disease. The piperazine derivatives of the invention to be tested were administered in a dose of 30 mg/kg at 3 hour in advance of the administration of $CCl_4$. For control group, 1.0% methylcellulose (MC) was administered in place of the piperazine derivative. For normal group, a simple olive oil was administered in place of the $CCl_4$-containing olive oil. For the administration, the piperazine derivative was employed in the form of a dispersion in aqueous MC solution (concentration: 1.0%).

At 24 hours after the administration of $CCl_4$, the rat was abdominally sectioned under ether anesthesia. From the abrominal large vein, a blood was collected. The collected blood was subjected to centrifugal separation at 3,000 r.p.m. for 10 min to obtain its plasma. The plasma was then analyzed in an autoanalyzer (Hitachi 705, tradename) for biochemically assaying GOT value and GPT value according to Karmen method.

The results are set forth in Table 4 in terms of a ratio (%) of suppression (prevention) of GOT or GPT. In Table 4, "*" means 90–100%, "" means 60–90%, and "*" means 30–60%. The number of the tested compound corresponds to the number set forth in Tables 1 and 2.

The ratio of suppression is calculated according to the following equation.

Ratio of suppresion = $[1 - \frac{\text{(value of sample-administered group } - \text{ value of normal group)}}{\text{(value of control group } - \text{ value or normal group)}}] \times 100$

TABLE 4

| No. of Compound | GOT | GPT |
| --- | --- | --- |
| 1 | • | • |
| 2 | • | — |
| 3 | •• | •• |
| 4 | ••• | ••• |
| 5 | ••• | ••• |
| 6 | ••• | ••• |
| 7 | •• | • |
| 9 | •• | •• |
| 10 | •• | • |
| 11 | ••• | ••• |
| 13 | • | • |
| 15 | ••• | ••• |
| 16 | ••• | ••• |
| 18 | •• | •• |
| 20 | •• | •• |
| 21 | •• | •• |
| 22 | ••• | •• |
| 23 | ••• | ••• |
| 31 | •• | • |
| 32 | •• | •• |
| 33 | ••• | •• |
| 34 | — | • |
| 35 | •• | •• |
| 37 | •• | •• |
| 38 | •• | •• |
| 44 | ••• | •• |
| 46 | ••• | ••• |
| 47 | ••• | ••• |
| 48 | •• | •• |
| 56 | ••• | ••• |
| 67 | • | • |
| 68 | •• | •• |
| 71 | •• | • |
| 73 | •• | •• |
| 75 | •• | •• |
| 93 | ••• | ••• |
| 100 | — | • |
| 110 | ••• | ••• |
| 113 | ••• | •• |
| 118 | •• | • |

When liver cells are damaged by the administration of CCl₄, enzymes contained in the celles are released into a blood, and various enzymic activities are observed in a serum obtained from the blood. Accordingly, it is known that a degree of damage of liver can be effectively determined by measuring serum transaminases such as GOT (glutamic-oxaloacetic transaminase) or GPT (glutamic-pyruvic transaminase). The above experiments were performed based on the above knowledge.

As is seen from the results of the above-given Experiment 2, the piperazine derivatives of the invention significantly well suppress increase of amounts of GOT and/or GPT which are known to indicate the degree of liver damage.

From the pharmacological experimental results given above, it is established that the piperazine derivatives of the invention show excellent inhibitory effect on lipid peroxidation, as well as effective preventive (or suppressive) action on deviation of values of GOT and/or GPT in acute liver damage model in vivo.

Further, it has been experimentally confirmed that all of piperazine derivatives of the invention tested for toxicity (Compound Nos. 4, 5, 22, 23, 32, 33, 38, 75 and 113 indicated in Tables 1 and 2) cause no death even at 1,600 mg/kg by oral administration.

The therapeutic agent of the present invention can be generally prepared in the form of a pharmaceutical composition in combination with an appropriate pharmaceutical carrier. Examples of the carrier include diluents such as filler, binder, disintegrating agent, and lubricant, vehicles, and excipients. The therapeutic agent of the invention can be orally or parenterally administered in the form of injection liquid, powder, capsules, granules, or pellets. The dose of the therapeutic agent of the invention varies with conditions and age of patients. Ordinarily, the piperazine derivative of the invention is administered into a patient at a dose of approx. 10 mg to 1 g per day.

Thus, the above-identified piperazine derivative having the formula (I) and its pharmaceutically acceptable salt show favorable action in in-vivo tests for treatment acute liver disease caused by carbon tetrachloride for inhibition or suppression of deviation of values of GOT (glutamic oxaloacetic transaminase) and GPT (glutamic pyruvic transaminase).

Accordingly, the piperazine derivative of the formula (I) and its pharmaceutically acceptable salt according to the invention are well effective for prevention or treatment (including treatment for suppression of disease) of liver disease. Further, the piperidine derivative of the formula (I) and its pharmaceutically acceptable salt show inhibitory effect on lipid peroxidation and are active as therapeutic agents for preventing or treating inflammation, rheumatism, disease of digestive tract.

The following examples further illustrate the present invention. In the examples, the compound number given at the end of each compound corresponds to the piperazine derivative set forth in Tables 1 and 2.

EXAMPLE 1 i) 3,4,5-Trimethoxybenzyl chloride

In 40 ml of benzene was dissolved 10 g of 3,4,5-trimethoxybenzyl alcohol. To the resulting solution was dropwise added under chilling with ice 10 ml of benzene solution containing 7.6 g of thionyl chloride. After the addition was complete, the mixture was stirred at room temperature for 15 min. The reaction solution was poured into a chilled aqueous potassium carbonate, and a separated benzene portion was collected. The benzene portion was washed with a saturated aqueous sodium chloride solution, dried over anhydrous sodium sulfate and placed under reduced pressure to distill off the solvent. The desired compound was obtained as a yellow solid (yield: 11.0 g).

ii) 1-(3,4,5-Trimethoxybenzyl)piperazine

A mixture of 4.48 g of piperazine (6 hydrates) and 10 ml of ethanol was warmed at 65°–70° C. to give a homogeneous solution. To the solution were added 4.09 g of piperazine?2HCl H₂O and 5 ml of ethanol. At the same temperature, 5.0 g of 3,4,5-trimethoxybenzyl chloride and 15 ml of ethanol were further added at once. The resulting mixture was stirred at 65°–70° C. for additional 30 min. and then chilled with ice. A precipitated insoluble was removed by filtration, and the resulting mother liquer was concentrated. To the concentrated mother liquer was added 8 ml of ethanolic 6-N hydrochloric acid. The mixture was stirred for 30 min under chilling with ice. Precipitated crystals were collected by filtration, washed with ethanol and dried to give hydrochloride of the desired compound.

The obtained hydrochloride was dissolved in 15 ml of water. The solution was made alkaline by addition of aqueous 1-N sodium hydroxide. The alkaline solution was extracted seven times with chloroform after salting-out. The chloroform extracts were combined, dried over anhydrous sodium sulfate, and placed under reduced pressure to distill off the solvent, to give 4.93 g of the desired compound as a pale yellow crystalline powder.

iii) Sodium 4-(3,4-5-trimethoxybenzyl)-1-piperazinecarbodithioate (Com. No. 89)

To 50 ml of ether solution containing 4.9 g of 1-(3,4,5-trimethoxybenzyl)piperazine was added under chilling with ice 1.01 g of sodium hydroxide in 1.5 ml of water. To the solution was further added dropwise under chilling with ice 13 ml of ether solution containing 1.81 g of carbon disulfide. The resulting mixture was stirred overnight at room temperature. Thus precipitated crystals were collected by filtration, washed with ether and dried under reduced pressure to give 6.67 g of the desired compound as a white powder, m.p. 119°–122° C.

$^1$H-NMR (CD$_3$OD) δ:2.30–2.60 (m, 4H), 3.46 (s, 2H), 3.76 (s, 3H), 3.84 (s, 6H), 4.3–4.6 (m, 4H), 6.64 (s, 2H).

IR (KBr) cm$^{-1}$: 3380, 1590, 1460, 1420, 1220, 1130.

EXAMPLE 2 i) Methyl 4-(3,4,5-trimethoxybenzyl)-1-piperazinecarbodithioate

To 70 ml of methanol containing 6.67 g of sodium 4-(3,4,5-trimethoxybenzyl)piperazinecarbodithioate was dropwise added under chilling with ice 20 ml of methanol solution containing 2.6 g of methyl iodide for 20 min. The resulting mixture was further stirred for 3 hours under chilling with ice. The reaction solution was placed under reduced pressure to distill off the solvent, leaving a residue. The residue was dissolved in water, and then extracted with chloroform. The chloroform portion was washed with a saturated aqueous sodium chloride solution, dried over anhydrous sodium sulfate, and placed under reduced pressure to distill off the solvent. Thus obtained crude product was purified by silica gel chromatography to give 3.7 g of the desired compound as a pale yellow crystalline product.

$^1$H-NMR (CDCl$_3$) δ:2.40–2.60 (m, 4H), 2.66 (s, 3H), 3.46 (s, 2H), 3.84 (s, 3H), 3.86 (s, 6H), 3.9–4.3 (m, 4H), 6.55 (s, 2H).

MS (m/e): 356 (M+), 341, 309.

ii) Methyl 4-(3,4,5-trimethoxybenzyl)-1-piperazinecarbodithioate.hydrochloride (Com. No. 41) m.p.: 212.5°–214° C. (decomp.).

$^1$H-NMR (CD$_3$OD) δ:2.65 (s, 3H), 3.1–3.7 (m, 6H), 3.78 (s, 3H), 3.90 (s, 6H), 4.33 (s, 2H), 4.9–5.5 (m, 2H), 6.94 (s, 2H).

IR (KBr) cm$^{-1}$: 2400, 1590, 1460, 1420, 1325, 1270, 1250, 1120, 950.

EXAMPLE 3

Methyl 4-(3,4,5-trihydroxybenzyl)-1-piperazinecarbodithioate (Com. No. 40)

To 100 ml of methylene dichloride was added 2.6 ml of boron tribromide, and the resulting mixture was chilled to −40° C. To this mixture was further dropwise added 50 ml of methylene chloride containing 2 g of 4-(3,4,5-trimethoxybenzyl)-1-piperazinecarbodithioate for approx. 30 min. The reaction mixture was stand for reaching room temperature, and stirred overnight at room temperature. To the mixture was then added portionwise water under chilling with ice. A resulting precipitate was collected, washed successively with water and acetone, and dried under reduced pressure at room temperature. The dried product was dissolved in a small amount of methanol. Water was added to the methanol solution to give a precipitate. The precipitate was collected by filtration and dried under reduced pressure to give 450 mg of hydrobromide of the desired compound as a pale red powder, m.p. 158°–160° C. (decomp.).

$^1$H-NMR (CD$_3$OD) δ:2.64 (s, 3H), 3.0–3.7 (m, 6H), 4.16 (s, 2H), 4.8–5.6 (m, 2H), 6.53 (s, 2H).

IR (KBr) cm$^{-1}$: 3125, 1625, 1545, 1450, 1420, 1340, 1255, 1025.

EXAMPLE 4

4-(3,4,5-Trimethoxybenzyl)-1-piperazinecarbodithioic acid (Com. No. 108)

In an aqueous 10% sodium hydroxide solution was dissolved 1.40 g (4.13 mmol.) of 3,4,5-trimethoxybenzyl-1-piperazine.dihydrochloride. The solution was then extracted with chloroform. The chloroform portion was dried over anhydrous sodium sulfate and placed under reduced pressure to distill off the solvent, to give 933 mg (yield: 90.3%) of a free amine product as a white crystalline product.

The obtained product was dissolved in 3 ml of methanol. The solution was stirred at room temperature for 1 hour after dropwise addition of 0.25 ml (4.1 mmol.) of carbon disulfide. Insolubles were removed by filtration and washed with methanol to give a pale yellow powder. The powder was then dried under reduced pressure to give 1,260 mg of the desired compound, m.p. 171°–174° C. (decomp.), yield 98.7%.

$^1$H-NMR (DMSO-d$_6$) δ:2.9–4.0 (m, 8H), 3.64, 3.77 (each s, 9H), 4.1–4.6 (m, 2H), 6.4–6.8 (m, 2H), 8.2–9.6 (br, 1H).

IR (KBr) cm$^{-1}$: 3400, 2980, 2960, 2920, 2895, 2820, 2645, 2575, 2500, 1585, 1495, 1460, 1440, 1435, 1420, 1380, 1360, 1350, 1340, 1320, 1250, 1240, 1230, 1200, 1175, 1150, 1120, 1100, 1060, 1020, 1005, 990, 980, 960, 940, 915, 835, 820.

EXAMPLE 5

Methyl 4-(3,4,5-triacetoxybenzyl)-1-piperazinecarbodithioate (Com. No. 42)

To 395 mg (1.0 mmol.) of methyl 4-(3,4,5-trihydroxybenzyl)-1-piperazinecarbodithioate was added 2 ml of dry pyridine. To the resulting suspension was added 0.22 ml (3.1 mmol.) of acetyl chloride under chilling with ice. The mixture was then stirred, and further stirred overnight at room temperature. The mixture was then extracted with ethyl acetate after addition of water. The extract was washed with a saturated aqueous sodium chloride solution, dried over anhydrous sodium sulfate and processed to distill off the solvent. The residue was purified by silica gel column chromatography and crystallized from ether to give 249 mg of the desired compound as a white crystalline product, m.p. 141°–143° C., yield 63.4%.

$^1$H-NMR (CDCl$_3$) δ:2.27 (s, 9H), 2.35–2.65 (m, 4H), 2.66 (s, 3H), 3.51 (s, 2H), 3.8–4.4 (m, 4H), 7.10 (s, 2H).

IR (KBr) cm$^{-1}$: 2930, 2905, 2800, 1775, 1495, 1470, 1420, 1360, 1215, 1205, 1200, 1180, 1165, 1130, 1045, 1000, 890.

EXAMPLE 6

Methyl 4-(5-acetoxy-2-hydroxybenzyl)-1-piperazinecarbodithioate (Com. No. 21)

To 5 ml of chloroform were added 152 mg of 4-acetoxyphenol, 211 mg of methyl 1-piperazinecarbodithioate and 36 mg of paraformaldehyde. The resulting mixture was refluxed for 4 hours. The mixture was cooled, and to this was added chloroform. The mixture was then washed with water and a saturated aqueous sodium chloride solution, dried over anhydrous sodium sulfate and placed under reduced pressure to distill of the solvent. The residue was purified by silica gel column chromatography to yield an oil. The oil was crystallized by addition of ethanol. The obtained crystals were collected by filtration to give 224 mg of the desired compound as a white crystalline product, m.p. 124° C., yield 65.9%.

$^1$H-NMR (CDCl$_3$) δ:2.24 (s, 3H), 2.66 (s, 3H), 2.3–2.8 (m, 4H), 3.68 (s, 2H), 4.0–4.4 (m, 4H), 6.6–7.0 (m, 3H).

IR (KBr) cm$^{-1}$: 2810, 1750, 1490, 1425, 1370, 1250, 1230, 1215, 1195, 1145.

EXAMPLE 7

Methyl 4-(2,3,4-trihydroxybenzyl)-1-piperazinecarbodithioate (Com. No. 32)

To a mixture of 0.15 ml (2.0 mmol.) of 37% formalin and 4 ml of methanol was dropwise added under stirring 2 ml of a methanol solution containing 353 mg (2.0 mmol.) of methyl 1-piperazinecarbodithoate. The resulting mixture was stirred overnight at room temperature without exposing to light, after addition of added 253 mg (2.0 mmol.) of pyrogallol. A precipitated solid was removed by filtration, and the solvent of the filtrate was evaporated. To the residue was added chloroform. After removing insolubles, the solvent was distilled off. The residual solid was then washed with hot ethanol to give 210 mg of the desired compound as a pale brown powder, yield 11.1%.

$^1$H-NMR (DMSO-d$_6$) δ:2.49 (s, 4H), 2.56 (s, 3H), 3.51 (s, 2H), 3.7–4.3 (br, 4H), 6.1–6.4 (m, 2H), 8.1–8.9 (br, 3H).

EXAMPLE 8

4-(3,4,5-Trihydroxybenzyl)-1-piperazinecarbodithioic acid (Com. No. 109)

In a nitrogen atmosphere, 1,033 mg (3.02 mmol.) of 4-(3,4,5-trimethoxybenzyl)-1-piperazinecarbodithioic acid was suspended in dry methylene chloride, and under chilling to −78° C. in a dry ice-acetone bath, to this was dropwise added 50 ml of methylene chloride solution containing 3 ml of boron tribromide. The mixture was left to slowly reach room temperature, and then stirred for 5 days at room temperature. To the reaction mixture was added water, and insolubles were removed by filtration. The insolubles were then washed with water, and thus obtained yellow solid was dissolved in methanol. The methanol solution was filtered to remove insolubles, and the solvent of the filtrate was distilled off. To the obtained yellow semi-oil was added ether, and insolubles were removed by filtration. The filtrate was dried and further purified by cellulose column chromatography (Avicel, trademark, eluent: butanol/acetic acid/water (10/1/1)). The eluate was treated to distill off the solvent (eluent). To the residue was added ether, and insolubles were removed by filtration. The solvent of the filtrate was distilled off, leaving 103 mg of the desired compound, m.p. higher than 250° C., yield 11.4%.

$^1$H-NMR (DMSO-d$_6$) δ:2.8–4.3 (m, 10H), 6.38 (s, 2H), 8.0–9.5 (br, 4H).

IR (KBr) cm$^{-1}$: 3400, 3325, 3105, 3000, 2920, 2840, 2760, 2700, 2550, 1610, 1530, 1450, 1430, 1395, 1380, 1330, 1300, 1235, 1190, 1160, 1150, 1070, 1035, 1005, 940, 860.

EXAMPLE 9

Methyl 4-(2,3,4-triacetoxybenzyl)-1-piperazinecarbodithioate (Com. No. 34)

In 520 ml of chloroform was suspended 50 g of methyl 4-(2,3,4-trihydroxybenzyl)-1-piperazinecarbodithioate, and to the suspension was dropwise added under chilling with ice 97.3 g of acetic anhydride over a period of 15 min. The mixture was then stirred for one hour. The reaction mixture was washed successively with water and a saturated aqueous sodium chloride solution, and dried over anhydrous sodium sulfate. The sodium sulfate was removed by filtration, and the filtrate was concentrated under reduced pressure. The residual oil was crystallized by addition of 250 ml of ethyl acetate. After stirring for one hour, the crystals were collected by filtration. The crystals were washed with ethyl acetate to give 48.8 g of the desired compound as white crystals, m.p. 148°–150° C. (decomp.), yield 69.7%.

$^1$H-NMR (CDCl$_3$) δ:2.27 (s, 9H), 2.3–2.6 (m, 4H), 2.65 (s, 3H), 3.44 (s, 2H), 3.8–4.3 (br, 4H), 7.13 (d, 1H, J=8.6 Hz), 7.28 (d, 1H, J=8.6 Hz).

IR (KBr) cm$^{-1}$: 2900, 2800, 1760, 1450, 1420, 1360, 1260, 1210, 1170, 1050, 1010, 910, 880, 820, 770.

EXAMPLE 10 i) Benzyl 1-piperazinecarbodithioate

To a solution of 0.8 g of sodium hydroxide in a mixture of 9 ml of methanol and 1.2 ml of water was added 3.0 g of 1-piperazinecarbodithioic acid. The mixture was stirred for 10 min., and placed under reduced pressure at a temperature below 50° C. to distill off methanol and water. To the residue was added 9 ml of methanol, and to the resulting solution was dropwise added under chilling with ice 3.1 g of benzyl bromide over a period of 20 min. The mixture was then stirred for 15 min at room temperature. Insolubles were removed by filtration, and the filtrate was placed under reduced pressure to distill off the solvent. The residue was extracted with ether. The ether extract was washed with water and an aqueous sodium chloride solution, dried over anhydrous sodium sulfate, and placed under reduced pressure to distill off the solvent and to give 3.13 g of the desired compound as a pale yellow oil, yield 67.0%.

$^1$H-NMR (CDCl$_3$) δ:1.72 (s, 1H), 2.6–3.1 (m, 4H), 4.05 (br, 4H), 4.57 (s, 2H), 6.9–7.6 (m, 5H).

IR (neat) cm$^{-1}$: 2950, 2900, 1460, 1420, 1250, 1220, 1130, 1020, 980, 750, 700.

ii) Benzyl 4-(2,3,4-trihydroxybenzyl)-1-piperazinecarbodithioate (Com. No. 100)

To a solution of 0.51 g of 35% formalin in 7.7 ml of ethanol was added under chilling with ice a solution of 1.5 g of benzyl 1-piperazinecarbodithioate in 7.5 ml of ethanol. The mixture was stirred at room temperature for 10 min. To the mixture was further added under chilling with ice a solution of 3.7 g of pyrogallol in 15.3 ml of ethanol at once. The mixture was then stirred for 2.5 hours at room temperature. Ethanol was evaporated under reduced pressure, and the residue was extracted with dichloromethane. The dichloromethane solution was washed with water and an aqueous sodium chloride solution, dried over anhydrous sodium sulfate, and placed under reduced pressure to distill off the solvent to give 2.17 g of the desired compound as a pale red powder, m.p. 125°–126° C. (decomp.), yield 92.9%.

$^1$H-NMR (CDCl$_3$) δ:2.4–2.8 (m, 4H), 3.64 (s, 2H), 4.14 (br, 4H), 4.52 (s, 2H), 6.11 (br, 3H), 7.0–7.4 (m, 7H).

EXAMPLE 11

4-(2,3,4-Trimethoxybenzyl)-1-piperazinecarbodithioic acid (Com. No. 93)

In 10 ml of methanol was dissolved 985 mg (3.7 mmol.) of trimethazidine, and to the mixture was dropwise added under stirring at room temperature 0.23 ml of carbon disulfide for 25 min. The mixture was further stirred for 5 hours at room temperature. A precipitate was collected by filtration and washed with methanol to give 1.11 g of the desired compound, m.p. 148°–150° C. (decomp.), yield 87.4%.

$^1$H-NMR (DMSO-d$_6$) δ:2.2–2.7 (m, 4H), 2.9–4.0 (m, 4H), 3.75 (s, 3H), 3.78 (s, 3H), 3.80 (s, 3H), 4.1–4.6 (m, 2H), 6.6–7.1 (m, 2H), 8.2–9.4 (br, 1H).

IR (KBr) cm$^{-1}$: 2975, 2900, 2810, 2780, 2700, 1600, 1490, 1460, 1440, 1410, 1380, 1350, 1320, 1290, 1280, 1250, 1230, 1200, 1180, 1090, 1040, 1000, 960, 940, 920, 890, 850, 800, 780, 750, 690.

EXAMPLE 12 i) Methyl 4-(2,3,4-trimethoxybenzyl)-1-piperazinecarbodithioate (Com. No. 33)

In a nitrogen atmosphere, 2.0 g of 4-(2,3,4-trimethoxybenzyl)-1-piperazinecarbodithioic acid, 0.26 g of granular sodium hydroxide, and 3 ml of methanol were mixed, and stirred at room temperature to yield a homogeneous reaction solution. To the solution was dropwise added under chilling with ice a solution of 0.39 ml of methyl iodide in 2.4 ml of methanol. After the addition was complete, the reaction solution was stirred for 2.5 hours at room temperature. The solvent was then distilled off under reduced pressure, and chloroform and water were added to the residue. The chloroform portion was separated, washed with a saturated aqueous sodium chloride solution, and dried over anhydrous sodium sulfate. The solvent was distilled off under reduced pressure to leave 2.0 g of the desired compound as a white powder, yield 97.9%.

$^1$H-NMR (CDCl$_3$) δ:2.4–2.7 (m, 4H), 2.65 (s, 3H), 3.51 (s, 2H), 3.86 (s, 3H), 3.87 (s, 6H), 3.8–4.3 (m, 4H), 6.63 (d, 1H, J=8.6 Hz), 6.97 (d, 1H, J=8.6 Hz).

ii) Methyl 4-(2,3,4-trimethoxybenzyl)-1-piperazinecarbodithioate hydrochloride

To 1.6 g of methyl 4-(2,3,4-trimethoxybenzyl)-1-piperazinecarbodithioate was dropwise added under chilling with ice 9 ml of 1-N hydrochloric acid-ethanol. The mixture was then stirred for 3 hours at room temperature. Precipitated crystals were collected by filtration and washed with ethanol to give 1.5 g of the desired hydrochloride as a white powder, m.p. 182°–184° C. (decomp.), yield 87.3%.

$^1$H-NMR (CDCl$_3$) δ:2.65 (s, 3H), 2.6–3.1 (m, 2H), 3.2–3.8 (m, 2H), 3.87 (s, 3H), 3.88 (s, 3H), 3.95 (s, 3H), 3.9–4.2 (m, 2H), 4.22 (br, 2H), 4.8–5.4 (m, 2H), 6.7 (d, 1H, J=8 Hz), 7.42 (d, 1H, J=8 Hz).

IR (KBr) cm$^{-1}$: 2900, 2450, 1600, 1500, 1460, 1400, 1300, 1270, 1220, 1120, 1100, 1020, 960, 820.

EXAMPLE 13 i) Isopropyl 4-(3,4,5-trimethoxybenzyl)-1-piperazinecarbodithioate (Com. No. 96)

In 2 ml of ethanol was suspended 364 mg of sodium 4-(3,4,5-trimethoxybenzyl)-1-piperazinecarbodithioate, and to the suspension was added 204 mg of isopropyl iodide. The resulting homogeneous solution was stirred overnight at room temperature. Ethanol was distilled off from the solution, and to the residue were added ether and water. The ether portion was taken out, washed with a saturated aqueous sodium chloride solution, dried over anhydrous sodium sulfate, and placed under reduced pressure to evaporate the solvent. The residue was purified by silica gel column chromatography to give 270 mg of the desired compound as a colorless oil, yield 70.3%).

$^1$H-NMR (CDCl$_3$) δ:1.41 (d, 6H, J=7 Hz), 2.3–2.7 (m, 4H), 3.45 (s, 2H), 3.8 and 3.85 (each s, 9H), 3.9–4.6 (m, 5H), 6.54 (s, 2H).

ii) Isopropyl 4-(3,4,5-trimethoxybenzyl)-1-piperazinecarbodithioate hydrochloride In 2 ml of chloroform was dissolved 250 mg of the above obtained product. To the solution was added 2 ml of 1-N hydrochloric acid-methanol. The solvent was then distilled off under reduced pressure. The residue was crystallized from ethanol/diethyl ether. The crystals were collected by filtration and washed with chilled ethanol and diethyl ether to give 230 mg of the desired compound as a white crystalline product, m.p. 210°–212° C., yield 84.1%.

$^1$H-NMR (CDCl$_3$) δ:1.44 (d, 6H, J=8 Hz), 2.5–3.1 (m, 2H), 3.3–4.4 (m, 7H), 3.84 and 3.92 (each s, 9H), 5.0–5.4 (m, 2H), 6.94 (s, 2H).

IR (KBr) cm$^{-1}$: 2510, 2410, 1590, 1455, 1425, 1400, 1330, 1275, 1255, 1120, 945.

EXAMPLE 14

Methyl 4-(2-hydroxy-5-methoxybenzyl)-1-piperazinecarbodithioate (Com. No. 20)

To 20 ml of ethanol was 1.05 g of 37% formalin, and to the mixture was added under chilling with ice 2.29 g of methyl 1-piperazinecarbodithioate. The mixture was then stirred for 30 min. at room temperature, and, after addition of 1.24 g of 4-methoxyphenol, refluxed overnight under heating. The solvent was distilled off under reduced pressure, and the residue was purified by silica gel column chromatography. The obtained oil was crystallized from 10 ml of ethanol. The crystals were collected by filtration and subsequently washed with ethanol to give 1.06 g of the desired compound as white crystals, m.p. 112° C., yield 34%.

$^1$H-NMR (CDCl$_3$) δ:2.65 (s, 3H), 2.5–2.8 (m, 4H), 3.68 (s, 2H), 3.73 (s, 3H), 3.9–4.4 (m, 4H), 6.4–6.9 (m, 3H), 9.5 (br, 1H).

IR (KBr) cm$^{-1}$: 1490, 1420, 1255, 1225, 1210, 1035, 995, 870, 735.

EXAMPLE 15

Methyl 4-(2,5-dihydroxybenzyl)-1-piperazinecarbodithioate hydrochloride (Com. No. 16)

In 38 ml of ethanol was suspended 10.6 g of methyl 4-(5-acetoxy-2-hydroxybenzyl)-1-piperazinecarbodithioate (compound prepared in Example 6). In a nitrogen atmosphere, 53 ml of conc. hydrochloric acid was added to the suspension at room temperature. After the solid was dissolved, insolubles were removed by filtration, and further the insolubles were washed with 4 ml of ethanol. The filtrate and washing were combined to give a pale brown solution. The solution was stirred for 20 hours at room temperature to give a suspension. The suspension was further stirred at 80° C. for 3 hours, and then stirred for 8 hours at room temperature. The crystalline solid was collected by filtration and washed with ethanol to give 6.34 g of the desired compound as a pale brown crystalline powder, m.p. 200°–202° C. (decomp.).

$^1$H-NMR (CD$_3$OD) δ:2.65 (s, 3H), 3.1–3.5 (m, 4H), 4.30 (s, 2H), 4.0–4.7 (m, 4H), 6.6–6.9 (m, 3H).

IR (KBr) cm$^{-1}$: 3200, 3000, 2830, 2700, 2580, 1500, 1450, 1435, 1415, 1380, 1335, 1320, 1260, 1230, 1200, 1190, 950, 835, 825.

EXAMPLE 16

Methyl 4-(2-hydroxy-3-methoxybenzyl)-1-piperazinecarbodithioate (Com. No. 18)

In 10 ml of ethanol was dissolved 0.86 g of 35% formalin. To the solution was dropwise added under chilling with ice a solution of 2.35 g of methyl 1-piperazinecarbodithioate in 5 ml of ethanol. The mixture was then stirred for 30 min. at room temperature. The mixture was refluxed overnight under heating after addition of a solution of 1.24 g of 2-methoxyphenol in 5 ml of ethanol under chilling with ice. The reaction mixture was cooled to room temperature. Precipitated crystals were collected by filtration and washed with 5 ml of ethanol to give 1.44 g of the desired compound as a white powder, m.p. 151°–152° C. (decomp.), yield 45.9%.

$^1$H-NMR (CDCl$_3$) δ:2.3–2.8 (m, 4H), 2.65 (s, 3H), 3.75 (s, 2H), 3.87 (s, 3H), 4.2 (br, 4H), 6.4–6.9 (m, 3H), 10 (br, 1H).

IR (KBr) cm$^{-1}$: 3450, 2580, 1580, 1460, 1420, 1230, 1140, 1070, 990, 960, 830, 770, 730.

EXAMPLE 17

Methyl 4-(6-propyloxycarbonyl-2,3,4-trihydroxybenzyl)-1-piperazinecarbodithioate (Com. No. 44)

In 10 ml of ethanol was dissolved 0.86 g (10 mmol.) of 35% formalin. To the solution placed in an ice bath was further added a solution of 1.94 g (10 mmol., purity 90.7%) of methyl 1-piperazinecarbodithioate in 4 ml of ethanol. The resulting mixture was then stirred for 30 min. at room temperature. To the mixture placed in an ice bath was dropwise added a solution of 2.12 g (10 mmol.) of propyl gallate in 4 ml of ethanol. The mixture was stirred overnight at room temperature and subsequently refluxed under heating for 4 hours. The mixture was cooled to room temperature. Precipitated crystals were collected by filtration and washed with ethanol to give 1.843 g of the desired compound as a grayish powder, m.p. 142°–144° C. (decomp.), yield 31.3%.

$^1$H-NMR (CDCl$_3$) δ:0.99 (t, 3H, J=7 Hz), 1.5–1.9 (m, 2H), 2.4–2.8 (m, 4H), 2.66 (s, 3H), 3.9–4.4 (m, 8H), 5.0–5.6 (br, 3H), 7.08 (s, 1H).

IR (KBr) cm$^{-1}$: 3380, 2960, 1700, 1600, 1460, 1420, 1340, 1260, 1230, 1100, 980, 780.

EXAMPLE 18 i) Methyl 4-(3,4-dimethoxy-2-hydroxybenzyl)-1-piperazinecarbodithioate (Com. No. 35)

In 10 ml of ethanol was dissolved 0.86 g of 35% formalin. To the solution was dropwise added under chilling with ice a solution of 2.35 g of methyl 1-piperazinecarbodithioate in 5 ml of ethanol. The mixture was then stirred for 30 min. at room temperature. The mixture was refluxed overnight under heating after addition of a solution of 1.54 g of 2,3-dimethoxyphenol in 5 ml of ethanol under chilling with ice. The reaction mixture was cooled to room temperature. The solvent was distilled off under reduced pressure, and the residue was purified by silica gel column chromatography. The eluate was treated with 10 ml of ethanol to obtain a crystalline product. The product was collected by filtration and washed with ethanol to give 1.76 g of the desired compound as a pale yellow crystalline product, m.p. 113° C. (decomp.), yield 51.5%.

$^1$H-NMR (CDCl$_3$) δ:2.4–2.9 (m, 4H), 2.66 (s, 3H), 3.69 (s, 2H), 3.84 (s, 3H), 3.88 (s, 3H), 4.2 (br, 4H), 6.35 (d, 1H, J=8 Hz), 6.64 (d, 1H, J=8 Hz).

ii) Methyl 4-(3,4-dimethoxy-2-hydroxybenzyl)-1-piperazinecarbodithioate hydrochloride In 1 ml of chloroform was dissolved 0.5 g of methyl 4-(3,4-dimethoxy-2-hydroxybenzyl)-1-piperazinecarbodithioate. To the solution was dropwise added under chilling with ice 1.46 ml of 1-N HCl/ether mixture, and the resulting mixture was stirred at room temperature. Precipitated crystals were collected by filtration and washed with 6 ml of ether to give 0.53 g of the desired compound as a white powder, m.p. 204°–205° C. (decomp.), yield 95.9%.

$^1$H-NMR (CDCl$_3$/CD$_3$OD) δ:2.66 (s, 3H), 2.8–3.2 (m, 2H), 3.4–4.2 (m, 4H), 3.86 (s, 3H), 3.88 (s, 3H), 4.28 (s, 2H), 4.9–5.4 (m, 2H), 6.55 (d, 1H, J=8.8 Hz), 7.25 (d, 1H, J=8.8 Hz).

IR (KBr) cm$^{-1}$: 3420, 2920, 2350, 1620, 1510, 1480, 1420, 1280, 1220, 1100, 1030, 950, 790.

EXAMPLE 19

Methyl 4-(2-hydroxybenzyl)-1-piperazinecarbodithioate (Com. No. 4)

In 10 ml of ethanol was dissolved 0.86 g of 35% formalin. To the solution was dropwise added under chilling with ice a solution of 2.35 g of methyl 1-piperazinecarbodithioate in 4 ml of ethanol. The mixture was then stirred for 30 min. at room temperature. The mixture was refluxed overnight under heating after addition of a solution of 2.82 g of phenol in 4 ml of ethanol under chilling with ice and subsequent stirring at room temperature for 3 hours. The reaction mixture was cooled to room temperature. A half amount of the solvent was distilled off under reduced pressure. To the residue was added 5 ml of ether to precipitate crystals. The crystals were collected by filtration and washed with 15 ml of ether to give 1.63 g of crude crystals of the desired compound. The crude crystals were then dissolved in chloroform. To the chloroform solution was added ethanol in twice amount of the amount of the chloroform. Precipitated crystals were collected by filtration to give 0.95 g of the desired compound as a white crystalline product, m.p. 147° C., yield 33.4%.

$^1$H-NMR (CDCl$_3$) δ:2.5–2.8 (m, 4H), 2.66 (s, 3H), 3.73 (s, 2H), 4.2 (br, 4H), 6.7–7.3 (m, 4H).

IR (KBr) cm$^{-1}$: 3400, 2820, 1580, 1420, 1270, 1250, 1220, 980, 920, 750.

EXAMPLE 20 i) Methyl 4-(2,3-dihydroxybenzyl)-1-piperazinecarbodithioate (Com. No. 15)

1.10 g of catechol, 2.11 g of methyl 1-piperazinecarbodithioate, 0.36 g of paraformaldehyde and 10 ml of chloroform were mixed and refluxed overnight under heating. The heated mixture was then cooled to room temperature, and impurities were removed. The chloroform portion was washed successively with water and a saturated aqueous sodium chloride solution, dried over anhydrous sodium sulfate, and placed under reduced pressure to distill off the solvent. The residue was purified by silica gel column chromatography and crystallized from ethanol. The obtained crystals (1.09 g) were dissolved in 4 ml of chloform. To the solution was added 8 ml of ethanol. Precipitated crystals were collected by filtration to give 0.94 g of the desired compound as a white crystalline product, yield 34.6%.

ii) Methyl 4-(2,3-dihydroxybenzyl)-1-piperazinecarbodithioate hydrochloride

In 3 ml of acetone was dissolved 250 mg of methyl 4-(2,3-dihydroxybenzyl)-1-piperazinecarbodithioate. To the solution was dropwise added under chilling with ice 0.84 ml of 1-N HCl/ether mixture, and the resulting mixture was stirred at room temperature. The solvent was distilled off under reduced pressure. The residue was stirred at room temperature with 2 ml of acetone. Precipitated crystals were collected by filtration and washed with 4 ml of acetone to give 213 mg of the desired compound as a white powder, m.p. 187°–189° C. (decomp.), yield 76.2%.

$^1$H-NMR (CD$_3$OD) δ:2.65 (s, 3H), 3.1–3.6 (br, 6H), 3.8–5.1 (m, 2H), 4.40 (s, 2H), 6.6–7.0 (m, 3H).

IR (KBr) cm$^{-1}$: 3460, 3260, 2580, 1600, 1480, 1400, 1280, 1240, 1210, 980, 730.

EXAMPLE 21 i) Methyl 4-(3,5-dimethoxy-4-hydroxybenzyl)-1-piperazinecarbodithioate (Com. No. 43)

In 10 ml of ethanol was dissolved 0.86 g of 35% formaline. To the solution was dropwise added under chilling with ice a solution of 2.35 g of methyl 1-piperazinecarbodithioate in 4 ml of ethanol. The resulting mixture was then stirred for 30 min. at room temperature. Under chilling with ice, a solution of 1.54 g of 2,6-dimethoxyphenol in 4 ml of ethanol was to the stirred mixture. The resulting mixture was stirred for one hour at room temperature, and then refluxed under heating for 38 hours. The refluxed mixture was then cooled to room temperature. Precipitated crystals were collected by filtration and then washed with ethanol to give 1.94 g of the desired compound a whilte crystalline product, yield 56.7%.

$^1$H-NMR (CDCl$_3$) δ:2.3–2.7 (m, 4H), 2.66 (s, 3H), 3.45 (s, 2H), 3.87 (s, 6H), 4.1 (s, 4H), 5.59 (s, 1H), 6.55 (s, 2H).

ii) Methyl 4-(3,5-dimethoxy-4-hydroxybenzyl)-1-piperazinecarbodithioate hydrochloride In 4 ml of chloroform was dissolved 500 mg of methyl 4-(3,5-dimethoxy-4-hydroxybenzyl)-1-piperazinecarbodithioate. To the solution was dropwise added under chilling with ice 1.46 ml of 1-N HCl/ether mixture. The solvent was then distilled off under reduced pressure. The residue was stirred overnight at room temperature together with 8 ml of ethyl acetate. Precipitated crystals were collected by filtration to give 529 mg of the desired compound as a white powder, m.p. 187°–188° C. (decomp.), yield 95.9%.

$^1$H-NMR (CD$_3$OD) δ:2.65 (s, 3H), 2.9–4.1 (m, 4H), 3.89 (s, 6H), 4.29 (s, 2H), 4.1–4.9 (m, 2H), 4.9–5.5 (m, 2H), 6.87 (s, 2H).

IR (KBr) cm$^{-1}$: 3400, 3100, 2520, 1610, 1510, 1460, 1420, 1330, 1270, 1240, 1210, 1110, 940.

EXAMPLE 22

Methyl 4-(5-formyl-2-hydroxy-3-methoxybenzyl)-1-piperazinecarbodithioate (Com. No. 38)

In 10 ml of ethanol was dissolved 0.86 g of 35% formalin. To the solution was dropwise added under chilling with ice a solution of 1.94 g of methyl 1-piperazinecarbodithioate in 4 ml of ethanol. The mixture was then stirred for 30 min. at room temperature. Under chilling with ice, a solution of 1.52 g of vanilline in 4 ml of ethanol was added to the reaction mixture. The mixture was stirred for 40 min. at room temperature and then refluxed under heating for 10 hours. The reaction mixture was cooled to room temperature to precipitate crystals. The crystals were collected and washed with ethanol to give 2.58 g of the desired compound as a white crystalline product, m.p. 144°–145° C. (decomp.), yield 75.8%.

$^1$H-NMR (CDCl$_3$) δ:2.4–2.8 (m, 4H), 2.66 (s, 3H), 3.84 (s, 2H), 3.95 (s, 3H), 3.9–4.4 (m, 4H), 7.1–7.4 (m, 2H), 9.78 (s, 1H).

IR (KBr) cm$^{-1}$: 3350, 2800, 1660, 1590, 1490, 1450, 1420, 1300, 1240, 1190, 1140, 1060, 990, 920, 860, 710.

EXAMPLE 23 i) Methyl 4-(6,7-dihydroxycumarin-8-yl)methyl-1-piperazinecarbodithioate (Com. No. 106)

To 10 ml of methanol were successively added 0.375 ml of 37% formalin, 882 mg (5 mmol.) of methyl 1-piperazinecarbodithionate, 891 mg (5 mmol.) of aesculetin (6,7-dioxycumarin) and 5 ml of methanol. The mixture was stirred for 2.5 hours at room temperature, and then refluxed under heating and stirring for 18 hours, to undergo a reaction. The reaction mixture was then cooled to deposit a precipitate. The precipitate was collected by filtration and washed successively with methanol, ethanol and n-hexane to give 1.36 g of the desired compound, yield 74.3%.

$^1$H-NMR (CDCl$_3$) δ:2.67 (s, 3H), 2.40–2.90 (m, 4H), 3.90–4.40 (m, 4H), 4.11 (s, 2H), 6.22 (d, 1H), 6.92 (s, 1H), 7.57 (d, 1H), 8.17 (s, 2H).

ii) Methyl 4-(6,7-dihydroxycumarin-8-yl)methyl-1-piperazinecarbodithioate hydrochloride The above obtained compound was dissolved in a mixture of methanol and chloroform. A methanol solution of hydrogen chloride gas was added to the resulting solution, to yield the desired hydrochloride, m.p. 217°–220° C. (decomp.).

$^1$H-NMR (CD$_3$OD) δ:2.64 (s, 3H), 3.00–3.60 (m, 4H), 4.53 (s, 2H), 4.00–4.60 (m, 4H), 6.21 (d, 1H), 7.09 (s, 1H), 7.83 (d, 1H).

IR (KBr) cm$^{-1}$: 3600–2300, 1700, 1610, 1570, 1400, 1290, 1260, 1210.

EXAMPLE 24

Methyl 4-{6-($\beta$-D-glucopyranosyloxy)-7-hydroxycumarin-8-yl}methyl-1-piperazinecarbodithioate (Com. No. 107)

To 10 ml of methanol were successively added 0.375 ml of 37% formalin, 0.88 g (5 mmol.) of methyl 1-piperazinecarbodithioate, 1.84 g (5 mmol.) of esculetin (-$\gamma$-esculetin-6-$\beta$-glucoside) and 5 ml of methanol. The mixture was stirred refluxed under heating and stirring for 4 hours, to undergo a reaction. The reaction mixture was then cooled to deposit a yellow syrup. The syrup was then separated from methanol by decantation and converted into a powdery deposit by addition of ether. The powdery deposit was collected by filtration and washed successively with ether and n-hexane to give 7.7 g of the desired compound, m.p. approx. 170° C. (decomp.).

$^1$H-NMR (DMSO-d$_6$) $\delta$:2.56 (s, 3H), 2.40–2.80 (m, 4H), 3.00–4.40 (m, 12H), 4.40–5.40 (m, 6H), 6.24 (d, 1H), 7.38 (s, 1H), 7.85 (d, 1H).

EXAMPLE 25

Methyl 4-(6,7-dihydroxycumarin-8-yl)methyl-1-piperazinecarbodithioate hydrochloride To 0.3 g of the product obtained in Example 23-i) was added 4.5 ml of 10% hydrochloric acid. The mixture was heated to 100°–110° C. for 80 min. The solvent was distilled off under reduced pressure. To the residue was added water. Insolubles were removed by filtration. The From the filtrate, the same hydrochloride as that of Example 23-ii) was obtained.

EXAMPLE 26 i) Methyl 4-{2-(3,4-dihydroxyphenyl)-2-oxo}ethyl-1-piperazinecarbodithioate (Com. No. 72)

In 2 ml of ethanol was dissolved 184 mg (1.044 mmol.) of methyl 1-piperazinecarbodithioate. To the resulting solution were added 195 mg (1.045 mmol) of 2-chloro-3',4'-dihydroxyacetophenone and 3 ml of ethanol. When the introduced solid material was dissolved in the mixture, 333 mg of sodium carbonate was added to the mixture. The mixture was then stirred for one hour at room temperature and then refluxed under heating and stirring for 3 hours. Ethanol was distilled off under reduced pressure, and 5 ml of water and 0.4 g of acetic acid were added to the residual gum. The gum was extracted with chloroform. The chloroform extract was dried over anhydrous sodium sulfate, placed under reduced pressure to distill off chloroform. The syrupy residue (0.3 g) was then crystallized from ethanol, collected by filtration, and washed successively with ethanol and n-hexane to give 0.13 g of the desired compound as a pale brown powder, m.p. 184°–186° C. (decomp.), yield 42.3%.

$^1$H-NMR (DMSO-d$_6$) $\delta$:2.40–2.90 (m, 4H), 2.57 (s, 3H), 3.80 (s, 2H), 3.86–4.50 (br, s, 4H), 6.79 (d, 1H, J=6.8 Hz), 7.10–7.50 (m, 2H).

IR (KBr) cm$^{-1}$: 3400, 2900, 1660, 1600, 1500, 1470, 1420, 1380, 1340, 1280, 1250, 1160, 1110.

ii) Methyl 4-{2-(3,4-dihydroxyphenyl)-2-oxo}ethyl-1-piperazinecarbodithioate hydrochloride The above obtained compound was dissolved in ethanol. A methanol solution of hydrogen chloride gas was added to the resulting solution. Methanol was distilled off under reduced pressure. Ether was added to the residue to give a precipitate. The precipitate was collected by filtration, washed with ether and n-hexane, and dried to yield the desired hydrochloride, m.p. 210° C. (decomp.).

$^1$H-NMR (CD$_3$OD) $\delta$:2.65 (s, 3H), 3.10–3.60 (m, 4H), 4.20–4.60 (m, 4H), 4.76 (s, 2H), 6.87 (d, 1H, J=9 Hz), 7.20–7.60 (m, 2H).

IR (KBr) cm$^{-1}$: 3600–2300, 1660, 1590, 1510, 1400, 1330, 1280, 1180, 1110, 1010, 960.

EXAMPLE 27 i) Methyl 4-{2-(3,4-dihydroxyphenyl)-2-hydroxy}ethyl-1-piperazinecarbodithioate (Com. No. 73)

To 1,025 mg (3.14 mmol.) of methyl 4-{2-(3,4-dihydroxyphenyl)-2-oxo}ethyl-1-piperazinecarbodithioate hydrochloride were added 56 ml of ethanol and 15 ml of tetrahydrofuran (THF). The mixture was chilled to −10° C., and 1.10 g of sodium borohydride was added to the mixture for 15 min. The mixture was then stirred at −10°-0° C. for 5 hours, and again chilled to −10° C. To the chilled mixture was added 1.78 g of acetic acid to decompose excessive sodium borohydride. The solvent was distilled off, and water was added to the residue to precipitate a gum. The gum was then extracted with ethyl acetate. The organic portion was taken out, washed with a saturated aqueous sodium chloride solution, dried over anhydrous sodium sulfate, and treated to distill off the solvent, to yield white crystals. The crystals were washed with ether, collected by filtration, and washed with n-hexane to give 0.59 g of the desired compound, yield 57.2%.

$^1$H-NMR (CD$_3$OD) $\delta$:2.20–2.90 (m, 6H), 2.61 (s, 3H), 3.90–4.30 (m, 4H), 4.67 (t, 1H, J=4 Hz), 6.50–6.90 (m, 3H).

IR (KBr) cm$^{-1}$: 3600–3000, 1590, 1500, 1410, 1270, 1220.

ii) Methyl 4-{2-(3,4-dihydroxyphenyl)-2-hydroxy}ethyl-1-piperazinecarbodithioate hydrochloride The above obtained compound was dissolved in methanol. A methanol solution of hydrogen chloride gas was added to the resulting solution. Methanol was distilled off under reduced pressure. The residue was washed with ether to yield the desired hydrochloride.

$^1$H-NMR (CD$_3$OD) $\delta$:2.64 (s, 3H), 2.70–3.40 (m, 6H), 4.10–4.50 (m, 4H), 4.60–5.00 (m, 1H), 6.60–6.90 (m, 3H).

IR (KBr) cm$^{-1}$: 3600–2300, 1600, 1510, 1450, 1400, 1270, 1220.

EXAMPLE 28 i) $\alpha$-Bromo-2,3,4-trimethoxyacetophenone 25 g of 2,3,4-trimethoxyacetophenone, 600 ml of ether and 240 ml of chloroform were mixed. To the resulting mixture was dropwise added under chilling with ice/sodium chloride mixture a solution of 19.18 g of bromine in 120 ml of chloroform for 3.3 hours. The resulting solution was washed successively with chilled water, chilled 5% aqueous sodium hydroxide solution, chilled water and aqueous sodium chloride solution, and dried over anhydrous sodium sulfate. Thereafter, the solvent was distilled off under reduced pressure at a temperature of lower than 50° C., leaving 33.0 g of yellow oil, yield 91.7%.

$^1$H-NMR (CDCl$_3$) $\delta$:3.86 (s, 3H), 3.92 (s, 3H), 4.05 (s, 3H), 4.56 (s, 2H), 6.73 (d, 1H, J=9 Hz), 7.60 (d, 1H, J=9 Hz).

IR (neat) cm$^{-1}$: 2950, 1680, 1490, 1410, 1290, 1210, 1110, 1000, 810.

ii) Methyl 4-{2-(2,3,4-trimethoxyphenyl)-2-oxo}ethyl-1-piperazinecarbodithioate (Com. No. 71)

16 g of α-bromo-2,3,4-trimethoxyacetophenone, 13.25 g of methyl 1-piperazinecarbodithioate, 17.6 g of sodium carbonate and 27.0 ml of ethanol were mixed and refluxed under heating for 5.5 hours. The hot reaction solution was filtered to remove the inorganic solid. The inorganic solid was washed with chloroform. The filtrate and the washing were combined and placed under reduced pressure to distill off the solvent. The obtained residue was extracted with chloroform. The chloroform extract was washed successively with water and an aqueous sodium chloride solution, and dried over anhydrous sodium sulfate. The solvent was distilled off under reduced pressure, leaving 26.5 g of a crystalline product. The crystalline product was recrystallized from 50 ml of ethanol to give 12.68 g of the desired compound as a pale brown needle-crystalline product, m.p. 96°–98° C., yield 59.7%.

$^1$H-NMR (CDCl$_3$) δ:2.5–2.8 (m, 4H), 2.66 (s, 3H), 3.84 (s, 2H), 3.86 (s, 3H), 3.91 (s, 3H), 3.98 (s, 3H), 4.22 (br, 4H), 6.72 (d, 1H, J=9 Hz), 7.53 (d, 1H, J=9 Hz).

IR (KBr) cm$^{-1}$: 3400, 2900, 2800, 1670, 1590, 1460, 1390, 1290, 1220, 1140, 1090, 1020, 1000, 980, 820.

EXAMPLE 29 i) Methyl 4-{2-(2,3,4-trimethoxyphenyl)ethyl}-1-piperazinecarbodithioate (Com. No. 67)

In a nitrogen atmosphere, 5 g of methyl 4-{2-(2,3,4-trimethoxyphenyl)-2-oxo}ethyl-1-piperazinecarbodithioate, 2.4 g of sodium borohydride and 4.7 g of anhydrous aluminum trichloride were mixed. To the mixture was then added 120 ml of dry tetrahydrofuran, and the resulting mixture was stirred for 6 hours. The mixture was chilled with ice. To the chilled mixture were added 48 ml of water. The aqueous mixture was extracted with ethyl acetate. The extract was washed with an aqueous sodium chloride solution, dried over anhydrous sodium sulfate, and placed under reduced pressure to distill off the solvent. An inorganic solid in the residue was removed by filtration. The extract was purified by silica gel column chromatography, to yield 1.18 g of the desired compound, yield 24.5%.

$^1$H-NMR (CDCl$_3$) δ:2.4–2.8 (m, 8H), 2.67 (s, 3H), 3.84 (s, 3H), 3.86 (s, 3H), 3.88 (s, 3H), 4.07 (br, 4H), 6.59 (s, 1H, J=8.4 Hz), 6.83 (s, 1H, J=8.4 Hz).

IR (neat) cm$^{-1}$: 2980–2825, 1730, 1600, 1490, 1460, 1410, 1270, 1215, 1130, 1095, 1050, 1005, 990, 925, 795.

ii) Methyl 4-{2-(2,3,4-trimethoxyphenyl)ethyl}-1-piperazinecarbodithioate hydrochloride In 2.0 ml of dichloromethane was dissolved 250 mg of the above-obtained product. Under chilling with ice, 0.67 ml of 1-N HCl/ether mixture was added to the resulting solution. The solvent was distilled off under reduced pressure. To the residue was added 1.6 ml of ethanol, and precipitated crystals were collected by filtration. The crystals were washed with 2 ml of ethanol to give 159 mg of the desired compound as a white powder, m.p. 202°–203° C., yield 58.2%.

$^1$H-NMR (CD$_3$OD) δ:2.67 (s, 3H), 2.6–3.2 (br, 2H), 2.9–3.3 (br. 4H), 3.3–4.3 (br, 4H), 3.84 (s, 6H), 3.92 (s, 3H), 4.9–5.4 (br, 2H), 6.59 (d, 1H, J=8.4 Hz), 6.92 (d, 1H, J=8.4 Hz).

IR (KBr) cm$^{-1}$: 3450, 2930, 2530, 2360, 1600, 1490, 1470, 1420, 1270, 1240, 1190, 1110, 1050, 960, 910, 800, 620.

EXAMPLE 30

Methyl 4-{2-(2,3,4-trihydroxyphenyl)ethyl}-1-piperazinecarbodithioate (Com. No. 68)

In 14 ml of dry dichloromethane was dissolved 1 ml of boron tribromide. 9.3 ml of the resulting solution containing 665 mmol. of boron tribromide was chilled to −50° C. in a nitrogen atmosphere. To the chilled solution was dropwise added a solution of 0.73 g of methyl 4-{2-(2,3,4-trimethoxyphenyl)ethyl}-1-piperazinecarbodithioate in 25 ml of dry dichloromethane for 15 min. The resulting mixture was left to reach room temperature, and then stirred overnight. To the mixture was added 3 ml of water, and further added a saturated aqueous sodium hydrogen carbonate solution until the mixture had pH 8. The mixture was then extracted with ethyl acetate. The extract was dried over anhydrous sodium sulfate and placed under reduced pressure to distill off the solvent, yielding 205 mg of the desired compound as a grayish powder, m.p. 156°–158° C. (decomp.), yield 31.5%.

$^1$H-NMR (CD$_3$OD) δ:2.63 (s, 3H), 2.5–2.9 (m, 8H), 4.0–4.4 (m, 4H) 6.23 (d, 1H, J=8.4 Hz) 6.33 (d, 1H, J=8.4 Hz).

IR (KBr) cm$^{-1}$: 3400, 2900, 1630, 1460, 1420, 1260, 1220, 1100, 1040, 920, 760, 610.

EXAMPLE 31 i) 1-(3,4,5-Trimethoxyphenyl)piperazine 11.9 g of 3,4,5-trimethoxyaniline, 11.6 g of bis-(2-chloroethyl)amine hydrochloride, 9 g of anhydrous potassium carbonate, and 48 ml of diglyme were mixed and refluxed under heating for 28 hours. The reaction mixture was cooled, and was added into 100 ml of water. A concentrated aqueous potassium hydroxide solution was added to the aqueous mixture until the mixture had pH 12. The aqueous solution was then extracted with ethyl acetate. The ethyl acetate portion was washed with water, dried over anhydrous sodium sulfate, and placed under reduced pressure to distill off the solvent. The residue was purified by silica gel column chromatography to give 2.37 g of the desired compound as a brown oil.

$^1$H-NMR (CDCl$_3$) δ:1.72 (s, 1H), 3.06 (s, 8H), 3.78 (s, 3H), 3.84 (s, 6H), 6.12 (s, 2H).

ii) 4-(3,4,5-Trimethoxyphenyl)-1-piperazinecarbodithioic acid (Com. No. 94)

In a nitrogen atmosphere, 1.9 g of 1-(3,4,5-trimethoxyphenyl)piperazine was dissolved in 10 ml of methanol. To the solution was dropwise added under chilling with ice 0.46 ml of carbon disulfide. After the addition was complete, the mixture was stirred at room temperature for 2 hours. Precipitated crystals were collected by filtration to give 1.9 g of the desired compound as a gray-brown powder, m.p. 183°–190° C. (decomp.), yield 77.7%.

$^1$H-NMR (DMSO-d$_6$) δ:2.9–3.4 (m, 7H), 3.57 (s, 3H), 3.75 (s, 6H), 4.4 (br, 2H), 6.21 (d, 2H, J=3.3 Hz).

IR (KBr) cm$^{-1}$: 2930, 2820, 1580, 1510, 1450, 1420, 1240, 1210, 1120, 1000, 930.

EXAMPLE 32

Methyl 4-(3,4,5-trimethoxyphenyl)-1-piperazinecarbodithioate (Com. No. 70)

In a nitrogen atmosphere, 1.5 g (4.6 mmol.) of 4-(3,4,5-trimethoxyphenyl)-1-piperazinecarbodithioic acid was suspended in methanol. After addition of 0.2 g of granular sodium hydroxide, the suspension was stirred at room temperature for one hour. The reaction mixture was chilled in a mixture of ice and sodium chloride. To the reaction mixture was dropwise added a solution of 0.29 ml of methyl iodide in 3.7 ml of methanol. After the addition was complete, the mixture was stirred at room temperature for 1 hour. Precipitated crystals were collected by filtration to give 0.8 g of the desired compound as a gray-brown powder, m.p. 135°–137° C. (decomp.), yield 50.8%.

$^1$H-NMR (CDCl$_3$) δ:2.69 (s, 3H), 3.1–3.3 (m, 4H), 3.79 (s, 3H), 3.85 (s, 6H), 4.31 (br, 4H), 6.16 (s, 2H).

IR (KBr) cm$^{-1}$: 1580, 1510, 1460, 1420, 1270, 1220, 1110, 980, 930, 820, 760.

EXAMPLE 33

Methyl 4-(1,4-benzoquinonylmethyl)-1-piperazinecarbodithioate (Com. No. 110)

In a mixture of 6.8 ml of 1-N hydrochloric acid and 6.8 ml of methanol was dissolved 680 mg of methyl 4-(2,5-dihydroxybenzyl)-1-piperazinecarbodithioate. The resulting solution was chilled with ice, and to this was dropwise added a solution of 1.24 g (5.3 mmol.) of FeCl$_3$.6H$_2$O in 4.3 ml of water for 15 min. To this was further added 25 ml of methanol. To thus obtained homogeneous solution was again added a solution of 2.2 g of FeCl$_3$.6H$_2$O in 10 ml of water. The mixture was then stirred for 10 min. and placed under reduced pressure to distill off methanol. To the residue was added 50 ml of chloroform, and to this was added a saturated sodium hydrogen carbonate to adjust pH of the mixture to 7. Insolubles were removed by filtration. The organic solvent portion was taken out, washed with water and a saturated aqueous sodium chloride solution, dried over anhydrous sodium sulfate, and placed under reduced pressure to distill off the solvent. The residue was then purified by silica gel column chromatography to give 234 mg of the desired compound as a yellow powder, m.p. 115°–116° C. (decomp.), yield 38.9%.

$^1$H-NMR (CDCl$_3$) δ:2.3–2.8 (m, 4H), 2.66 (s, 3H), 3.40 (d, 2H, J=2 Hz), 3.9–4.4 (m, 4H), 6.6–6.9 (m, 3H).

IR (KBr) cm$^{-1}$: 3420, 1650, 1465, 1420, 1290, 1230, 995, 910.

EXAMPLE 34 i) Methyl 4-[(2,5-dihydroxy-3,4,6-trimethyl)benzyl]-1-piperazinecarbodithioate (Com. No. 46)

In 30 ml of ethanol was dissolved 2.58 g (30 mmol.) of 35% formalin. Under chilling with ice, to the solution was dropwise added a solution of 5.88 g (30 mmol., purity 90%) of methyl 1-piperazinecarbodithioate in 15 ml of ethanol. The mixture was then stirred for 30 min. at room temperature. To the mixture was dropwise added under chilling with ice a solution of 4.57 g (30 mmol.) of 2,3,5-trimethylhydroquinone in 30 ml of ethanol. The mixture was stirred at room temperature for 30 min. The mixture was refluxed under heating for approx. 35 hours and subsequently treated to distill off the solvent. To the residue was added ether. Thus obtained precipitate was collected by filtration to give 3.13 g of the desired compound as a pale brown powder, yield 30.6%.

$^1$H-NMR (CDCl$_3$) δ:2.15 (s, 9H), 2.40–2.7 (m, 7H), 3.70 (s, 2H), 3.9–4.4 (m, 4H).

ii) Methyl 4-[(2,5-dihydroxy-3,4,6-trimethyl)benzyl]-1-piperazinecarbodithioate hydrochloride In 10 ml of chloroform was dissolved 0.5 g (6.47 mmol.) of the above-obtained product. Under chilling with ice, 1.47 ml of 1-N HCl/ether mixture was added to the resulting solution. The solvent was distilled off under reduced pressure. To the residue was added 6 ml of acetone, and precipitated crystals were collected by filtration to give 0.35 g of the desired compound as a white powder, m.p. 166°–169° C. (decomp.), yield 70.0%.

$^1$H-NMR (CD$_3$OD/CDCl$_3$=3/1) δ: 2.20 (s, 6H), 2.30 (s, 3H), 2.67 (s, 3H), 3.1–3.6 (br, 4H), 3.6–4.1 (br, 2H), 4.46 (s, 2H), 4.8–5.3 (br, 2H).

IR (KBr) cm$^{-1}$: 3300, 2900, 2600, 1700, 1605, 1455, 1400, 1250, 1210, 1190, 1110, 1075, 1020, 930.

EXAMPLE 35

Methyl 4-(3,5,6-trimethyl-1,4-benzoquinonylmethyl)-1-piperazinecarbodithioate (Com. No. 113)

In a mixture of 10 ml of 1-N hydrochloric acid and 16 ml of methanol was dissolved 1,020 mg (3 mmol.) of methyl 4-[(2,5-dihydroxy-3,4,6-trimethyl)benzyl]-1-piperazinecarbodithioate. The resulting solution was chilled with ice, and to this was dropwise added a solution of 1.86 g (7.95 mmol.) of FeCl$_3$.6H$_2$O in 6.4 ml of water for 5 min. To this was further added a solution of 1.86 g (7.95 mmol.) of FeCl$_3$.6H$_2$O in 6.4 ml of water. The mixture was stirred and then treated to distill off methanol. To the residue was added 75 ml of chloroform and further added an aqueous sodium hydrogen carbonate, until the mixture was neutralized. A precipitated redbrown solid was removed by filtration, and the organic portion was taken out. The organic portion was washed with water and a saturated sodium chloride solution, dried over anhydrous sodium sulfate, and placed under reduced pressure to distill off the solvent. The residue was crystallized from ethanol, and the crystals were collected by filtration to give 840 mg of the desired compound as an orange powder, m.p. 133°–135° C.

$^1$H-NMR (CDCl$_3$) δ:2.03 (s, 6H), 2.13 (s, 3H), 2.4–2.6 (m, 4H), 2.65 (s, 3H), 3.45 (s, 2H), 3.9–4.2 (m, 4H).

IR (KBr) cm$^{-1}$: 3400, 2900, 2790, 1630, 1620 (shoulder), 1460, 1420, 1365, 1280, 1255, 1220, 1135, 1020, 990, 950, 915.

EXAMPLE 36 i) 3,4-Dimethoxybenzyl chloride

In a nitrogen atmosphere, 5 g (29.73 mmol.) of 3,4-dimethoxybenzyl alcohol was dissolved in 25 ml of dichloromethane. The obtained solution was placed in an ice-bath, and to this was dropwise added a solution of 2.16 ml (29.74 mmol.) of thionyl chloride in 5 ml of methylene chloride. The mixture was then stirred at room temperature for 1 hour. The mixture was placed under reduced pressure at room temperature to distill off the solvent to give 5.624 g of the desired compound as a yellow oil.

¹H-NMR (CDCl₃) δ:3.86 (s, 3H), 3.88 (s, 3H), 4.57 (s, 2H), 6.7–7.0 (m, 3H).

ii) Methyl 4-(3,4-dimethoxybenzyl)-1-piperazinecarbodithioate (Com. No. 31)

In a nitrogen atmosphere, 5.615 g (30.08 mmol.) of 3,4-dimethoxybenzyl chloride, 5.57 g (30.08 mmol., purity 95%) of methyl 1-piperazinecarbodithioate, 3.19 g (30.08 mmol.) of anhydrous sodium carbonate and 50 ml of ethanol were mixed and refluxed under heating for 5.5 hours. The solvent was distilled off under reduced pressure. To the residue were added 20 ml of dichloromethane and 20 ml of water. The organic solvent portion was taken out and washed with 30 ml of 1-N hydrochloric acid. To the organic portion was added 1-N aqueous sodium hydroxide solution. The organic solvent portion was again taken out and dried over anhydrous sodium sulfate. The solvent was distilled off under reduced pressure. To the residue was added 20 ml of ethanol. Precipitated crystals were collected by filtration and washed with ethanol to give 1.465 g of methyl 4-(3,4-dimethoxybenzyl)-1-piperazinecarbodithioate, yield 14.9%.

iii) Methyl 4-(3,4-dimethoxybenzyl)-1-piperazinecarbodithioate hydrochloride

In 2.5 ml of ethanol was suspended 1 g (3.06 mmol.) of the above-obtained crystals. To the suspension was dropwise added under chilling with ice 0.51 g of 6-N HCl in ethanol. The solvent was distilled off under reduced pressure, and 3 ml of ethanol was added to the residue. Precipitated crystals were collected by filtration to give 0.866 g of the desired compound as a white powder, m.p. 138°–140° C. (decomp.), yield 78.1%.

¹H-NMR (CDCl₃) δ:2.65 (s, 3H), 2.6–3.1 (m, 2H), 3.2–3.7 (m, 2H), 3.89 (s, 3H), 3.97 (s, 3H), 3.9–4.3 (m, 4H), 4.9–5.5 (m, 2H), 6.6–7.1 (m, 2H), 7.3–7.6 (m, 1H).

IR (KBr) cm⁻¹: 2920, 2520, 2440, 1630, 1590, 1520, 1460, 1410, 1265, 1240, 1220, 1160, 1140, 1110, 1020, 950.

EXAMPLE 37

Methyl 4-(2-dimethylaminobenzyl)-1-piperazinecarbodithioate (Com. No. 13)

In 20 ml of acetone, 2.06 g (10 mmol.) of 2-dimethylaminobenzyl chloride hydrochloride, 1.76 g (10 mmol.) of methyl piperazinecarbodithioate, and 1.06 g (10 mmol.) of sodium carbonate were stirred overnight at room temperature. Acetone was distilled off under reduced pressure. Water was added to the residue. The aqueous mixture was extracted with ether. The ether portion was washed with water and a saturated aqueous sodium chloride solution, dried over anhydrous sodium sulfate, and placed under reduced pressure to distill of the solvent. The residue was purified by means of silica gel column and then recrystallized from ether to give 1.32 g of the desired compound as a white crystalline product, m.p. 90°–91° C., yield 42.7%.

¹H-NMR (CDCl₃) δ:2.4–2.8 (m, 4H), 2.64 (s, 3H), 2.68 (s, 6H), 3.62 (s, 2H), 3.8–4.4 (m, 4H), 6.8–7.5 (m, 4H).

IR (KBr) cm⁻¹: 2820, 1450, 1425, 1265, 1230, 1185, 1135, 1125, 1040, 990, 940, 760, 720.

EXAMPLE 38 i) 2,3-Dimethoxybenzyl chloride

In 30 ml of methylene chloride was dissolved 3.36 g (20 mmol.) of 2,3-dimethoxybenzyl alcohol. Under chilling with ice, to the solution was dropwise added a solution of 1.6 ml (22 mmol.) of thionyl chloride in 5 ml of methylene chloride for 10 min. The mixture was stirred at the same temperature and then placed under reduced pressure to distill off the solvent, to give 3.71 g of 2,3-dimethoxybenzyl chloride as a brown oil, yield 99.5%.

ii) Methyl 4-(2,3-dimethoxybenzyl)-1-piperazinecarbodithioate (Com. No. 22)

To 20 ml of ethanol were added 1.0 g (5.36 mmol) of 2,3-dimethoxybenzyl chloride, 943 mg (5.36 mmol.) of methyl 1-piperazinecarbodithioate and 568 mg (5.36 mmol.) of sodium carbonate. The obtained mixture was refluxed under heating for 2 hours. Ethanol was distilled off under reduced pressure. To the residue was added water. The aqueous mixture was extracted with 30 ml of ether. The ether portion was shaken together with 5 ml of 3-N hydrochloric acid. An oil which was insoluble in either portion and the aqueous portion were combined. The combined mixture was extracted with ether, after addition of 20 ml of 1-N aqueous sodium hydroxide solution. The ether extract was washed with water and a saturated aqueous sodium chloride solution, dried over anhydrous sodium sulfate, and placed under reduced pressure to distill off the solvent. The residue was recrystallized from ethanol to give 708 mg of the desired compound, m.p. 110°–111° C., yield 40.5%.

¹H-NMR (CDCl₃) δ:2.4–2.7 (m, 4H), 2.64 (s, 3H), 3.59 (s, 2H), 3.82 and 3.86 (each s, 6H), 3.9–4.4 (m, 4H), 6.7–7.1 (m, 3H).

IR (KBr) cm⁻¹: 1480, 1425, 1255, 1225, 1135, 1065, 1005, 995, 780.

EXAMPLE 39

Methyl 4-(2,5-dihydroxy-3,4-dimethoxy-6-methylbenzyl)-1-piperazinecarbodithioate (Com. No. 47)

In 28 ml of ethanol was dissolved 1.82 g (10 mmol.) of 2,3-dimethoxy-5-methyl-1,4-benzoquinone. To the solution was portionwise added at room temperature 240 mg (6.3 mmol.) of sodium borohydride. The mixture was stirred for 15 min. The mixture was then made acidic by addition of 3-N hydrochloric acid. To the mixture were added 50 ml of water and 100 ml of ether for performing extraction. The ether portion was washed with water and a saturated aqueous sodium chloride solution, dried over anhydrous sodium sulfate, and placed under reduced pressure to distill off the solvent to give 1.72 g of 2,3-dimethoxy-5-methylhydroquinone as a yellow oil, yield 93.5%. To the resulting oil were added 1.65 g (9.3 mmol.) of methyl 1-piperazinecarbodithioate and 280 mg (9.3 mmol.) of paraformaldehyde. The mixture was added to 17 ml of chloroform, and the resulting mixture was refluxed under heating for 6 hours. To the heated mixture was added water. The aqueous mixture was then extracted with chloroform. The chloroform extract was washed with water and a saturated aqueous sodium chloride solution, dried over anhydrous sodium sulfate, and placed under reduced pressure to distill off the solvent. The residue was dissolved in 10 ml of ethanol. Insolubles were removed by filtration. The filtrate was placed under reduced pressure to distill off ethanol. The residue was then purified by means of silica gel column, to give 1.1 g of a pale yellow oil, yield 31.8%. The oil was crystallized from ethanol. The crystals were collected by filtration to give 790 mg of the desired compound as a yellow crystalline product, m.p. 135°–136° C.

¹H-NMR (CDCl₃) δ:2.11 (s, 3H), 2.66 (s, 3H), 2.5–2.8 (m, 4H), 3.72 (s, 2H), 3.9 and 3.95 (each s, 6H), 4.0–4.4 (m, 4H).

IR (KBr) cm⁻¹: 3450, 2950, 1465, 1420, 1380, 1270, 1230, 1190, 1120, 1090, 1055, 1050, 985, 965, 920.

EXAMPLE 40

Methyl 4-(5,6-dimethoxy-3-methyl-1,4-benzoquinonylmethyl)-1-piperazinecarbodithioate (Com. No. 118)

To 700 mg (1.88 mmol.) of methyl 4-(2,5-dihydroxy-3,4-dimethoxy-6-methylbenzyl)-1-piperazinecarbodithioate were added 7 ml of 1-N hydrochloric acid and 17 ml of methanol. The mixture was chilled with ice, and to the mixture was dropwise added a solution of 1.76 g (7.52 mmol.) of FeCl₃·6H₂O in 5 ml of water. The resulting homogeneous red-colored solution was stirred for 30 min. and placed under reduced pressure at a temperature of lower than 50° C. to distill off methanol. To the residue was added 50 ml of ethyl acetate, and further added portionwise a saturated aqueous sodium hydrogen carbonate solution to adjust the solution to pH 10. A precipitated brownish red solid was removed by filtration. Thus obtained organic filtrate was washed with water and a saturated aqueous sodium chloride solution, dried over anhydrous sodium sulfate, and placed under reduced pressure to distill off the solvent. The residue was crystallized from ethanol, and collected by filtration, to give 540 mg of the desired compound as an orange-brown crystalline powder, m.p. 115°–116° C., yield 77.6%.

¹H-NMR (CDCl₃) δ:2.11 (s, 3H), 2.4–2.8 (m, 4H), 2.64 (s, 3H), 3.42 (s, 2H), 3.8–4.3 (m, 4H), 4.00 (s, 6H).

IR (KBr) cm⁻¹: 1670, 1640, 1615, 1410, 1260, 1230, 1195, 1150, 990.

EXAMPLE 41 i) Methyl 4-[(4,6-dimethoxy-2-hydroxy)benzyl]-1-piperazinecarbodithioate (Com. No. 37)

In 10 ml of ethanol was dissolved 0.86 g (10 mmol.) of 35% formaline. Under chilling with ice, to the solution was dropwise added a solution of 2.35 g (10 mmol., purity 75%) of methyl 1-piperazinecarbodithioate in 5 ml of ethanol. The mixture was stirred at room temperature for 30 min. To the mixture was then dropwise added under chilling with ice a solution of 1.54 g (10 mmol.) of 3,5-dimethoxyphenol in 5 ml of ethanol. The resulting suspension was then stirred at room temperature for 30 min. The suspension was refluxed under heating for 30 min., and allowed to cool spontaneously. Precipitated crystals were collected by filtration, washed with 20 ml of ethanol, and dried under reduced pressure, to give 1.345 g of a crude product. The mother liquer was concentrated, and the resulting residue was crystallized from 10 ml of ethanol. The crystals were washed and dried to give 1.26 g of second crystals, yield 76.1%.

¹H-NMR (CDCl₃) δ:2.66 (s, 3H), 2.4–2.8 (m, 4H), 3.73 (s, 3H), 3.76 (s, 5H), 3.9–4.4 (m, 4H), 5.9–6.1 (m, 2H).

ii) Methyl 4-[(4,6-dimethoxy-2-hydroxy)benzyl]-1-piperazinecarbodithioate hydrochloride In 2 ml of chloroform was dissolved 0.50 g (1.46 mmol.) of the above-obtained product. To the solution was added 1.46 ml of 1-N HCl in ether. The mixture was placed under reduced pressure to distill off the solvent. The residue was crystallized from 8 ml of acetone and collected by filtration, to give 0.48 g of the desired compound as a white crystalline product, m.p. 153°–154° C. (decomp.), yield 86.8%.

¹H-NMR (CDCl₃) δ:2.65 (s, 3H), 3.0–3.6 (m, 6H), 3.78 (s, 3H), 3.87 (s, 3H), 4.34 (s, 2H), 4.4–5.2 (m, 2H), 6.16 (s, 2H).

IR (KBr) cm⁻¹: 3070, 2930, 2560, 1620, 1590, 1510, 1460, 1420, 1270, 1220, 1200, 1150, 1120, 1100, 940, 820.

EXAMPLE 42 i) 2-Methoxybenzyl chloride

In a nitrogen atmosphere, 2.00 g (14.5 mmol.) of 2-methoxybenzyl alcohol was dissolved in 10 ml of dichloromethane. The obtained solution was placed in an ice-bath, and to this was dropwise added a solution of 1.06 ml (14.6 mmol.) of thionyl chloride in 2 ml of dichloromethane.

The mixture was then stirred at room temperature for 1.5 hours. The mixture was placed under reduced pressure at room temperature to distill off the solvent to give 2.32 g of the desired compound as a yellow oil.

¹H-NMR (CDCl₃) δ:3.87 (s, 3H), 4.64 (s, 2H), 6.7–7.4 (m, 4H).

ii) Methyl 4-(2-methoxybenzyl)-1-piperazinecarbodithioate (Com. No. 5)

In a nitrogen atmosphere, 2.28 g (14.5 mmol.) of 2-methoxybenzyl chloride, 2.69 g (14.5 mmol., purity 94.8%) of methyl 1-piperazinecarbodithioate, 1.53 g (14.5 mmol.) of anhydrous sodium carbonate and 15 ml of ethanol were mixed and refluxed under heating for 18 hours. Insolubles were removed by filtration, and the solvent of the filtrate was distilled off under reduced pressure. To the residue were added 15 ml of dichloromethane and 15 ml of water. The organic solvent portion was taken out, washed with 17 ml of 1-N hydrochloric acid and 20 ml of 1-N aqueous sodium hydroxide solution, and dried over anhydrous sodium sulfate. The solvent was distilled off under reduced pressure. The residue was purified by column chromatography to give 1.92 g of methyl 4-(2-methoxybenzyl)-1-piperazinecarbodithioate, yield 44.7%.

iii) Methyl 4-(2-methoxybenzyl)-1-piperazinecarbodithioate hydrochloride

In 5.5 ml of ethanol was suspended 0.87 g (2.95 mmol.) of the above-obtained crystals. To the suspension was dropwise added under chilling with ice 0.5 ml of 6-N HCl in ethanol. The solvent was distilled off under reduced pressure, and 3 ml of ether was added to the residue. Precipitated crystals were collected by filtration and washed with 5 ml of ether to give 0.81 g of the desired compound as a white powder, m.p. 216°–217° C. (decomp.), yield 82.0%.

¹H-NMR (CD₃OD) δ:2.65 (s, 3H), 3.2–4.0 (m, 6H), 3.94 (s, 3H), 4.42 (s, 2H), 4.8–5.4 (m, 2H), 6.9–7.6 (m, 4H).

IR (KBr) cm⁻¹: 2920, 2510, 2450, 1605, 1495, 1460, 1410, 1250, 1210, 1110, 1040, 1020, 950, 760.

EXAMPLE 43 i) 2,5-Dimethoxybenzyl chloride

In a nitrogen atmosphere, 2.00 g (11.9 mmol.) of 2,5-dimethoxybenzyl alcohol was dissolved in 10 ml of dichloromethane. The obtained solution was placed in an ice-bath, and to this was dropwise added a solution of 0.87 ml (12.0 mmol.) of thionyl chloride in 2 ml of dichloromethane. The mixture was then stirred at room temperature for 1.5 hour. The mixture was placed under reduced pressure at room temperature to distill off the solvent to give 2.22 g of the desired compound as a pale yellow oil.

$^1$H-NMR (CDCl$_3$) δ:3.76 (s, 3H), 3.81 (s, 3H), 4.59 (s, 2H), 6.7-7.0 (m, 3H).

ii) Methyl 4-(2,5-dimethoxybenzyl)-1-piperazinecarbodithioate (Com. No. 23)

In a nitrogen atmosphere, 2.20 g (11.8 mmol.) of 2,5-dimethoxybenzyl chloride, 2.19 g (11.8 mmol.) of methyl 1-piperazinecarbodithioate, 1.25 g (11.8 mmol.) of anhydrous sodium carbonate and 15 ml of ethanol were mixed and refluxed under heating for 18 hours. Insolubles were removed by filtration. The solvent of the filtrate was distilled off under reduced pressure. To the residue were added 15 ml of dichloromethane and 15 ml of water. The organic solvent portion was taken out, washed with 15 ml of 1-N hydrochloric acid and 18 ml of 1-N aqueous sodium hydroxide solution, and dried over anhydrous sodium sulfate. The solvent was then distilled off under reduced pressure. The residue was purified by column chromatography to give 1.23 g of methyl 4-(2,5-dimethoxybenzyl)-1-piperazinecarbodithioate, yield 31.9%.

iii) Methyl 4-(2,5-dimethoxybenzyl)-1-piperazinecarbodithioate hydrochloride

In 5 ml of ethanol was suspended 0.76 g (2.31 mmol.) of the above-obtained crystals. To the suspension was dropwise added under chilling with ice 0.4 ml of 6-N HCl in ethanol. The solvent was distilled off under reduced pressure, and 3 ml of ether was added to the residue. Precipitated crystals were collected by filtration and washed with 5 ml of ether to give 0.53 g of the desired compound as a white powder, m.p. 195°-197° C. (decomp.), yield 62.8%.

$^1$H-NMR (CD$_3$OD) δ:2.66 (s, 3H), 3.2-3.7 (m, 6H), 3.79 (s, 3H), 3.89 (s, 3H), 4.39 (s, 2H), 4.9-5.4 (m, 2H), 7.0-7.1 (m, 3H).

IR (KBr) cm$^{-1}$: 2990, 2950, 2830, 2500, 2360, 1500, 1470, 1405, 1280, 1260, 1225, 1045, 1020, 960, 805.

EXAMPLE 44 i) Methyl 4-diphenylmethyl-1-piperazinecarbodithioate (Com. No. 102)

In 25 ml of methanol was dissolved 5.00 g (19.8 mmol.) of 1-benzhydrylpiperazine. To the solution was dropwise added under chilling with ice a solution of 1.51 g (19.8 mmol.) of carbon disulfide in 5 ml of methanol. The mixture was then stirred for 30 min. Under chilling with ice, to the stirred mixture was added a solution of 3.80 g (19.8 mmol.) of 28%-sodium methylate-in-methanol solution. The mixture was then stirred until the mixture gave a clear solution. To this was added a solution of 2.90 g (19.8 mmol.) of 97%-iodomethane in 5 ml of methanol. The mixture was then stirred at room temperature for 1.5 hours. Precipitated crystals were collected by filtration and washed with methanol, to give 5.78 g of methyl 4-diphenylmethyl-1-piperazinecarbodithioate.

ii) Methyl 4-diphenylmethyl-1-piperazinecarbodithioate hydrochloride

In 1.4 ml of chloroform was dissolved 0.70 g (2.04 mmol.) of the above-obtained crystals. Under chilling with ice, to the solution were added 2.1 ml of 1-N HCl/ether solution and 2 ml of chloroform. The mixture was stirred at room temperature for 1 hours. Precipitated crystals were collected by filtration and washed with chloroform/ether (1/1), to give 0.71 g of the desired compound as a white powder, m.p. 216°-218° C. (decomp.), yield 91.7%.

$^1$H-NMR (CD$_3$OD) δ:2.64 (s, 3H), 3.2-3.6 (m, 4H), 3.8-5.2 (m, 4H), 5.46 (s, 1H), 7.3-7.9 (m, 10H).

IR (KBr) cm$^{-1}$: 2410, 1620, 1470, 1450, 1410, 1275, 1225, 1205, 1120, 1020, 1000, 940, 920, 750, 700.

EXAMPLE 45 i) Methyl 4-(2-methylthiobenzyl)-1-piperazinecarbodithioate (Com. No. 9)

In 20 ml of ethanol, 2.1 g (12.2 mmol.) of 2-methylthiobenzyl chloride, 2.17 g (12.3 mmol.) of methyl 1-piperazinecarbodithioate and 1.30 g (12.3 mmol.) of sodium carbonate were refluxed under heating for 2 hours. Ethanol was distilled off under reduced pressure. The residue was extracted with ether, after addition of water. The ether portion was washed with water and a saturated aqueous sodium chloride solution, dried over anhydrous sodium sulfate, and placed under reduced pressure to distill off the solvent. The residue was purified over silica gel column, to give 1.18 g of the desired compound as a yellow oil, yield 31%.

$^1$H-NMR (CDCl$_3$) δ:2.44 (s, 3H), 2.4-2.7 (m, 4H), 2.64 (s, 3H), 3.58 (s, 2H), 3.8-4.4 (m, 4H), 6.9-7.5 (m, 4H).

ii) Methyl 4-(2-methylthiobenzyl)-1-piperazinecarbodithioate hydrochloride

To 11 ml of methylene chloride was added the above-obtained oil. To the mixture was added 2 ml of 6-N HCl in ethanol. The solvent was distilled off under reduced pressure, and 10 ml of ethyl acetate was added to the residue. Precipitated crystals were collected by filtration to give 910 mg of the desired compound as a white crystalline powder, m.p. 204°-208° C. (decomp.), yield 74%.

$^1$H-NMR (CDCl$_3$/CD$_3$OD, ¼, v/v) δ:2.55 (s, 3H), 2.66 (s, 3H), 3.2-3.7 (m, 4H), 3.7-4.2 (m, 2H), 4.56 (s, 2H), 4.8-5.4 (m, 2H), 7.2-7.8 (m, 4H).

IR (KBr) cm$^{-1}$: 2350, 1460, 1420, 1270, 1215, 1110, 1035, 1010, 955, 765.

EXAMPLE 46

Methyl 4-(2,3,4-trimethoxyphenylacetyl)-1-piperazinecarbodithioate (Com. No. 75)

In 6.2 ml of methylene chloride were dissolved 310 mg (1.37 mmol.) of 2,3,4-trimethoxyphenylacetic acid and 289 mg (1.64 mmol.) of methyl 1-piperazinecarbodithioate. To the solution was added 395 mg (1.92 mmol.) of dicyclohexylcarbodiimide. The mixture was stirred at room temperature for 1 hour. A precipitated solid was removed by filtration, and to the filtrate were added methylene chloride and 1-N hydrochloric acid. The organic solvent portion was taken out, washed with a saturated aqueous sodium chloride solution, dried over anhydrous sodium sulfate, and placed under reduced pressure to distill off the solvent. The residue was purified over a silica gel column. The obtained oil was crystallized from a mixture of ethanol and hexane, yielding 257 mg of the desired compound as a white crystalline product, m.p. 119°-120° C., yield 48.8%.

$^1$H-NMR (CDCl$_3$) δ:2.65 (s, 3H), 3.66 (s, 2H), 3.3-4.3 (m, 8H), 3.8-3.9 (m, 9H), 6.58 and 6.88 (each d, 2H, J=9 Hz).

IR (KBr) cm$^{-1}$: 1630, 1490, 1460, 1420, 1275, 1240, 1215, 1090, 1045, 1010, 950.

EXAMPLE 47 i) Methyl 4-(2-nitrobenzyl)-1-piperazinecarbodithioate (Com. No. 10)

To 30 ml of ethanol were added 3.43 g (20 mmol.) of 2-nitrobenzyl chloride, 3.52 g (20 mmol.) of methyl 1-piperazinecarbodithioate, and 2.12 g (20 mmol.) of sodium carbonate. The mixture was then stirred for 4 hours at room temperature and further stirred overnight at 50°-60° C. Ethanol was distilled off under reduced pressure, and the residue was extracted using water and chloroform. The organic solvent portion was washed with water and a saturated aqueous sodium chloride solution, dried over anhydrous sodium sulfate, and placed under reduced pressure to distill off the solvent. The residue was crystallized from 40 ml of ether, collected by filtration and washed with ether, to give 4.3 g of the desired compound, as a yellow crystalline product, yield 69.1%.

$^1$H-NMR (CDCl$_3$) δ:2.52 (t, 4H, J=5 Hz), 2.64 (s, 3H), 3.83 (s, 2H), 3.9-4.4 (m, 4H), 7.2-7.9 (m, 4H).

ii) Methyl 4-(2-nitrobenzyl)-1-piperazinecarbodithioate hydrochloride

In 2 ml of methylene chloride was dissolved 500 mg (1.61 mmol.) of the above-obtained crystalline product. To the mixture was added 2 ml of 6-N HCl in ethanol. The solvent was distilled off under reduced pressure. 2 ml of ethyl acetate was added to the residue to precipitate crystals. The crystals were collected by filtration to give 497 mg of the desired compound as a white crystalline product, m.p. 208°-211° C. (decomp.), yield 88.8%.

$^1$H-NMR (DMSO-d$_6$) δ:2.61 (s, 3H), 3.0-3.5 (m, 4H), 3.7-4.9 (m, 4H), 4.59 (s, 3H), 7.5-8.2 (m, 4H).

IR (KBr) cm$^{-1}$: 2320, 1520, 1460, 1400, 1335, 1270, 1195, 945.

EXAMPLE 48

Methyl 4-(2-aminobenzyl)-1-piperazinecarbodithioate (Com. No. 11)

To a mixture of 4 ml of conc. hydrochloric acid and 4 ml of ethanol was added 622 mg (2.0 mmol.) of methyl 4-(2-nitrobenzyl)-1-piperazinecarbodithioate. The mixture was chilled with ice, and then to this chilled mixture was dropwise added under stirring a solution of 2.7 g (12 mmol.) of SnCl$_2$.2H$_2$O in 5 ml of ethanol for 15 min. After the addition was complete, the mixture was further stirred at room temperature for 2 hours. Ethanol was distilled off under reduced pressure, and to the residue were added 10 ml of water and 10 ml of ethyl acetate. The resulting mixture was made alkaline by addition of saturated aqueous sodium hydrogen carbonate solution. Precipitated insolubles were removed by filtration. The organic filtrate was washed with a saturated aqueous sodium chloride solution, dried over anhydrous sodium sulfate, and placed under reduced pressure to distill off the solvent. The residue was crystallized from ether, and collected by filtration, yielding 436 mg of the desired compound as a white crystalline product, m.p. 110°-113.5° C., yield 77.6%.

$^1$H-NMR (CDCl$_3$) δ:2.50 (t, 4H, J=6 Hz), 2.65 (s, 3H), 3.53 (s, 2H), 4.10 (br, 4H), 4.54 (br, 2H), 6.5-7.2 (m, 4H).

IR (KBr) cm$^{-1}$: 3450, 3300, 2800, 1605, 1405, 1280, 1260, 1240, 1225, 1145, 990, 925, 740.

EXAMPLE 49 i) Methyl 4-(2,5-diacetoxy-3,4-dimethoxy-6-methylbenzyl)-1-piperazinecarbodithioate (Com. No. 48)

In a nitrogen atmosphere, 0.50 g (1.34 mmol.) of methyl 4-(2,5-dihydroxy-3,4-dimethoxy-6-methylbenzyl)-1-piperazinecarbodithioate was dissolved in 5 ml of dichloromethane. To the resulting solution was added 0.30 g (2.96 mmol.) of triethylamine. The solution was then chilled with ice, and to the chilled solution was dropwise added a solution of 0.25 g (2.96 mmol.) of 95%-acetyl chloride in 3 ml of dichloromethane. The mixture was then stirred for 6 hours. To the mixture were then added 10 ml of dichloromethane and a small amount of a saturated aqueous sodium hydrogen carbonate solution. The mixture was well shaken, and the organic solvent portion was taken out. The organic portion was dried over anhydrous sodium sulfate and placed under reduced pressure to give 0.63 g of methyl 4-(2,5-diacetoxy-3,4-dimethoxy-6-methylbenzyl)-1-piperazinecarbodithioate as an oil.

ii) Methyl 4-(2,5-diacetoxy-3,4-dimethoxy-6-methylbenzyl)-1-piperazinecarbodithioate hydrochloride In 10 ml of dichloromethane was dissolved 0.63 g (1.38 mmol.) of the above oil. The solution was chilled with ice, and to the chilled solution was introduced gaseous hydrogen chloride. The solvent was distilled off under reduced pressure. The obtained residue was crystallized from a mixture of 4 ml of ether, a small amount of acetone and 2 ml of dichloromethane. The precipitated crystals were collected by filtration to give 0.54 g of the desired compound as a white powder, m.p. 194°-195° C. (decomp.), yield 79.7%.

$^1$H-NMR (CDCl$_3$) δ:2.34 (s, 3H), 2.35 (s, 3H), 2.43 (s, 3H), 2.66 (s, 3H), 2.8-3.6 (m, 4H), 3.84 (s, 3H), 3.8-5.3 (m, 4H), 3.88 (s, 3H), 4.20 (s,2H).

IR (KBr) cm$^{-1}$: 3000, 2950, 2500, 2420, 1750, 1605, 1475, 1450, 1410, 1370, 1350, 1270, 1250, 1200, 1170, 1105, 1060, 1010, 950, 940, 910, 880.

EXAMPLE 50

Methyl 4-(2,3,4-trimethoxybenzoyl)-1-piperazinecarbodithioate (Com. No. 56)

In a nitrogen atmosphere, 10 ml (138 mmol.) of thionyl chloride was added to 1.00 g (4.71 mmol.) of 2,3,4-trimethoxybenzoic acid. The mixture was refluxed under heating for 2 hours. The solvent was distilled off under reduced pressure. To the residue was added 10 ml of dry benzene, and the mixture was placed under reduced pressure to distill off benzene. This procedure was repeated once. To the residue was dropwise added at room temperature a solution of 0.88 g (4.74 mmol., purity 95%) of methyl 1-piperazinecarbodithioate in 12 ml of dichloromethane. In the course of the addition, 0.48 g (4.74 mmol.) of triethylamine was added to the mixture. The resulting mixture was then stirred overnight. The reaction mixture was washed successively with 1-N hydrochloric acid and a saturated aqueous sodium chloride solution, dried over anhydrous sodium sulfate, and placed under pressure to distill off the solvent. The residue was crystallized from acetone. The crystals were collected by filtration. The filtrate was concentrated, and additional crystals were further precipitated from the concentrated filtrate by addition of a small amount of ethanol. These crystalline portions were combined to give 0.90 g of the desired compound as a white crystalline product, m.p. 149°-150° C. (decomp.), yield 51.6%.

$^1$H-NMR (CDCl$_3$) δ:2.67 (s, 3H), 3.2-3.6 (m, 2H), 3.6-3.9 (m, 2H), 3.88 (s, 9H), 3.9-4.4 (m, 4H), 6.70 (d, 1H, J=8.6 Hz), 6.98 (d, 1H, J=8.6 Hz).

IR (KBr) cm$^{-1}$: 2930, 2830, 1620, 1595, 1495, 1475, 1450, 1425, 1365, 1280, 1235, 1215, 1180, 1155, 1095, 1040, 1000, 925, 900, 820, 810, 750, 700.

EXAMPLE 51 i) Methyl 4-(2-chlorobenzyl)-1-piperazinecarbodithioate (Com. No. 2)

In 16 ml of ethanol, 1.61 g (10 mmol.) of 2-chlorobenzyl chloride, 1.76 g (10 mmol.) of methyl 1-piperazinecarbodithioate and 1.06 g (10 mmol.) of sodium carbonate were heated to reflux for 4 hours. Ethanol was distilled off under reduced pressure, and to the residue was added water. The aqueous mixture was extracted with 30 ml of ether. The ether extract was shaken with 15 ml of 3N-hydrochloric acid. There were separated three layers. The aqueous portion and the oil portion were taken out and combined. The combined mixture was made alkaline with 1-N aqueous sodium hydroxide solution and extracted with ether. The ether portion was washed with a saturated aqueous sodium chloride solution, dried over anhydrous sodium sulfate, and placed under reduced pressure to distill off the solvent. The residue was purified over a silica gel column to give 1.03 g of methyl 4-(2-chlorobenzyl)-1-piperazinecarbothioate as a pale brown oil, yield 34.3%.

$^1$H-NMR (CDCl$_3$) δ:2.5-2.8 (m, 4H), 2.66 (s, 3H), 3.64 (s, 2H), 3.9-4.3 (m, 4H), 7.1-7.5 (m, 4H).

ii) Methyl 4-(2-chlorobenzyl)-1-piperazinecarbodithioate hydrochloride

In 20 ml of ethyl acetate was dissolved 0.98 g of the above-obtained product. To the solution was added 1.5 ml of 6-N hydrochloric acid in ethanol, and the mixture was stirred. Precipitated crystals were collected by filtration and washed with ethyl acetate to give 900 mg of the desired compound as a pale yellow crystalline product, m.p. 235° C. (decomp.)

$^1$H-NMR (CDCl$_3$/CD$_3$OD=6/1) δ:2.63 (s, 3H), 2.8-4.2 (m, 6H), 4.47 (s, 2H), 4.9-5.5 (m, 2H), 7.2-8.1 (m, 4H).

IR (KBr) cm$^{-1}$: 2700-2100, 1465, 1410, 1265, 1245, 1215, 1195, 1110, 955, 745.

EXAMPLE 52 i) Methyl 4-(4-methoxybenzyl)-1-piperazinecarbodithioate (Com. No. 7)

In a nitrogen atmosphere, 2.00 g (14.5 mmol.) of 4-methoxybenzyl alcohol was dissolved in 10 ml of dichloromethane. Under chilling with ice, to the solution was dropwise added a solution of 1.05 ml (14.5 mmol.) of thionyl chloride in 2 ml of dichloromethane. The mixture was then stirred at room temperature for 1 hour. The solvent was distilled off under reduced pressure. The residue was mixed with 2.90 g (14.5 mmol., purity 88.1%) of methyl 1-piperazinecarbodithioate, 1.54 g (14.5 mmol.) of anhydrous sodium carbonate and 25 ml of ethanol. The mixture was refluxed under heating for 14.5 hours. The solvent was distilled off under reduced pressure. The residue was mixed with 10 ml of dichloromethane and 10 ml of water. The mixture was allowed to give separated layers, and filtered to remove insolubles. The organic solvent portion was washed with water and a saturated aqueous sodium chloride solution, dried over anhydrous sodium sulfate, and placed under reduced pressure to distill off the solvent. The residue was purified over a silica gel column to give 1.46 g of methyl 4-(4-methoxybenzyl)-1-piperazinecarbodithioate as a pale yellow oil, yield 33.9%.

ii) Methyl 4-(4-methoxybenzyl)-1-piperazinecarbodithioate hydrochloride

In 5.8 ml of dichloromethane was dissolved 1.46 g (2.92 mmol.) of the above-obtained oil. Under chilling with ice, to the solution was dropwise added 4.92 ml of 1-N HCl/ether solution, and the mixture was stirred. Precipitated crystals were collected by filtration and washed with 5 ml of ether to give 1.43 g of the desired compound as a white crystalline powder, m.p. 205°-206° C. (decomp.), yield 87.4%.

$^1$H-NMR (CD$_3$OD) δ:2.65 (s, 3H), 3.0-4.0 (m, 6H), 3.83 (s, 3H), 4.34 (s, 2H), 4.9-5.6 (m, 2H), 7.02 (d, 2H, J=8.8 Hz), 7.49 (d, 2H, J=8.8 Hz).

IR (KBr) cm$^{-1}$: 2900, 2830, 2650, 2520, 2450, 1610, 1580, 1510, 1460, 1405, 1300, 1270, 1250, 1210, 1175, 1120, 1105, 1025, 945, 845, 820.

EXAMPLE 53 i) Methyl 4-(3-methoxybenzyl)-1-piperazinecarbodithioate (Com. No. 6)

In a nitrogen atmosphere, 1.57 g (10.0 mmol.) of 3-methoxybenzyl chloride, 2.00 g (10.0 mmol., purity 88.1%) of methyl 1-piperazinecarbodithioate, 1.06 g (10.0 mmol.) of anhydrous sodium carbonate and 20 ml of ethanol. The mixture was refluxed under heating for 5 hours. The solvent was distilled off under reduced pressure. The residue was mixed with 15 ml of dichloromethane and 10 ml of water. The mixture was allowed to give separated layers. The organic solvent portion was washed with water and a saturated aqueous sodium chloride solution, dried over anhydrous sodium sulfate, and placed under reduced pressure to distill off the solvent. The residue was purified over a silica gel column to give 2.46 g of methyl 4-(3-methoxybenzyl)-1-piperazinecarbodithioate as a colorless crystalline product, yield 82.8%.

ii) Methyl 4-(3-methoxybenzyl)-1-piperazinecarbodithioate hydrochloride

In 20 ml of ethyl acetate was dissolved 2.31 g (7.79 mmol.) of the above-obtained product. Under chilling with ice, to the solution was dropwise added 2.0 ml of 6-N hydrochloric acid in ethanol, and the mixture was stirred. Precipitated crystals were collected by filtration and washed with 10 ml of ethyl acetate to give 1.63 g of the desired compound as a white crystalline powder, m.p. 183°-184° C. (decomp.), yield 62.9%.

$^1$H-NMR (CD$_3$OD) δ:2.65 (s, 3H), 2.6-3.7 (m, 4H), 3.86 (s, 3H), 3.9-4.4 (m, 4H), 4.9-5.5 (m, 2H), 6.8-7.5 (m, 4H).

IR (KBr) cm$^{-1}$: 3050, 2990, 2910, 2830, 2660, 2500, 2420, 1600, 1580, 1490, 1460, 1410, 1370, 1340, 1295, 1260, 1250, 1200, 1190, 1170, 1120, 1070, 1030, 1000, 950, 860, 795, 775, 740, 690.

EXAMPLE 54 i) Methyl 4-(2-methylbenzyl)-1-piperazinecarbodithioate (Com. No. 3)

1.405 g (10 mmol.) of 2-methylbenzyl chloride, 1.76 g (10 mmol.) of methyl 1-piperazinecarbodithioate, 1.06 g (10 mmol.) of anhydrous sodium carbonate and 14 ml of ethanol. The mixture was refluxed under heating for 2.5 hours. Ethanol was distilled off under reduced pressure. The residue was mixed with water and ether. The organic solvent portion was taken out, and to the portion was added 15 ml of 3-N hydrochloric acid. The aqueous portion was neutralized with 1-N aqueous sodium hydroxide solution, and extracted with ethyl acetate. The ethyl acetate portion was washed with water and a saturated aqueous sodium chloride solution, dried over anhydrous sodium sulfate, and placed under reduced pressure to distill off the solvent. The residue was purified over a silica gel column to give 790 mg of methyl 4-(2-methylbenzyl)-1-piperazinecarbodithioate as a white crystalline product, yield 28.2%.

$^1$H-NMR (CDCl$_3$): 2.36 (s, 3H), 2.51 (t, 4H, J=5 Hz), 2.64 (s, 3H), 3.48 (s, 2H), 3.8-4.4 (m, 4H), 7.0-7.4 (m, 4H).

ii) Methyl 4-(2-methylbenzyl)-1-piperazinecarbodithioate hydrochloride

In 7 ml of ethyl acetate was dissolved 670 mg (2.39 mmol.) of the above-obtained product. To the solution was added 1.0 ml of 6-N HCl in ethanol, and the mixture was stirred. Precipitated crystals were collected by filtration and washed with of ethyl acetate to give 610 mg of the desired compound as a colorless crystalline product, m.p. 214° C. (decomp.), yield 80.6%.

$^1$H-NMR (CD$_3$OD/CDCl$_3$=3/1): 2.49 (s, 3H), 2.67 (s, 3H), 2.8-4.2 (m, 6H), 4.38 (s, 2H), 4.9-5.4 (m, 2H), 7.1-7.8 (m, 4H).

IR (KBr) cm$^{-1}$: 2700-2200, 1470, 1430, 1400, 1270, 1210, 1020, 955, 755.

PREPARATION EXAMPLE 1

Powder

| Piperazine derivative of the invention | 10 wt. parts |
|---|---|
| Heavy magnesium oxide | 10 wt. parts |
| Lactose | 80 wt. parts |

The above compounds were mixed homogeneously and pulverized to prepare a powder.

PREPARATION EXAMPLE 2

Powder

| Piperazine derivative of the invention | 10 wt. parts |
|---|---|
| Synthetic aluminum silicate | 10 wt. parts |
| Calcium hydrogenphospate | 5 wt. parts |
| Lactose | 75 wt. parts |

The above compounds were mixed homogeneously and pulverized to prepare a powder.

PREPARATION EXAMPLE 3

Granules

| Piperazine derivative of the invention | 50 wt. parts |
|---|---|
| Starch | 10 wt. parts |
| Lactose | 15 wt. parts |
| Crystalline cellulose | 20 wt. parts |
| Polyvinyl alcohol | 5 wt. parts |
| Water | 30 wt. parts |

The above compounds were mixed and kneaded homogeneously, dried, pulverized and sieved to prepare granules.

PREPARATION EXAMPLE 4

Pellets 99 parts by weight of the granules of Preparation Example 3 were mixed with one part of calcium stearate, and the mixture was pelletized under pressure to give a pellet of diameter of 10 mm.

PREPARATION EXAMPLE 5

Injection Solution

| Piperazine derivative of the invention | 0.5 wt. part |
|---|---|
| Nonionic surface active agent | 2.5 wt. parts |
| Physiological saline solution | 97 wt. parts |

The above compounds were mixed and sanitized to prepare the injection solution.

PREPARATION EXAMPLE 6

Capsules

The powder of Preparation Example 1 is charged in a commercially available capsule case to give capsules.

We claim:

1. A method of treatment of liver disease in humans comprising administering to a patient an anti-liver disease effective amount of a piperazine having the formula:

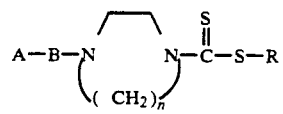

wherein
A represents a phenyl group which may have at least one substituent selected from the group consisting of halogen, alkyl fluoroalkyl, formyl, alkoxycarbonyl, acyl, hydroxy, alkoxy, acyloxy, glycosyloxy, amino, alkylamino, mercapto, alkylthio and nitro;
B represents a single bond or a straight chain alkylene group containing 1-4 carbon atoms which may have at least one substituent selected from the group consisting of alkyl, non-heterocyclic aryl, non-heterocyclic aralkyl, hydroxy and oxo;
R represents an atom or a group selected from the group consisting of hydrogen, alkali metal, alkaline earth metal, alkyl, cycloalkyl, non-heterocyclic aralkyl and non-heterocyclic aryl; and
n is 2 or 3,
or it pharmaceutically acceptable salt.

2. The method of claim 1 wherein A is a phenyl group having at least one substituent selected from the group consisting of hydroxy, alkoxy, acyloxy, amino, alkylamino, alkylthio, halogen, alkyl and nitro.

3. The method of claim 1 wherein A is a phenyl group having at least one substituent selected from the group consisting of hydroxy and alkoxy and further having at least one substituent selected from the group consisting of halogen, alkyl, fluoroalkyl, formyl, alkoxycarbonyl, acyl, acyloxy, glycosyloxy, amino, alkylamino, mercapto, alkylthio and nitro.

4. The method of claim 1 wherein B is a straight chain alkylene group having 1-4 carbon atoms which may have at least one substituent selected from the group consisting of phenyl, benzyl, hydroxy and oxo.

5. The method of claim 1 wherein R is alkyl.

6. The method of claim 1 wherein the dosage is from 10 mg to 1 g per day.

* * * * *